(12) United States Patent
Kassab et al.

(10) Patent No.: US 8,167,896 B2
(45) Date of Patent: May 1, 2012

(54) DEVICES, SYSTEMS, AND METHODS FOR ORGAN RESTRICTION

(75) Inventors: Ghassan Kassab, Zionsville, IN (US); Jose Navia, Sr., Buenos Aires (AR)

(73) Assignee: CVDevices, LLC, Zionsville, IN (US)

( * ) Notice: Subject to any disclaimer, the term of this patent is extended or adjusted under 35 U.S.C. 154(b) by 0 days.

(21) Appl. No.: 12/602,467

(22) PCT Filed: Feb. 28, 2008

(86) PCT No.: PCT/US2008/055303
§ 371 (c)(1),
(2), (4) Date: Nov. 30, 2009

(87) PCT Pub. No.: WO2008/147582
PCT Pub. Date: Dec. 4, 2008

(65) Prior Publication Data
US 2010/0174295 A1     Jul. 8, 2010

Related U.S. Application Data

(60) Provisional application No. 60/940,627, filed on May 29, 2007, provisional application No. 60/940,630, filed on May 29, 2007.

(30) Foreign Application Priority Data

Jun. 29, 2007    (WO) ................ PCT/US2007/015238

(51) Int. Cl.
*A61B 17/10* (2006.01)
(52) U.S. Cl. .................. 606/142; 606/151; 606/157
(58) Field of Classification Search .................. 606/139, 606/142, 151, 157, 143, 213, 220, 219, 232; 600/37
See application file for complete search history.

(56) References Cited

U.S. PATENT DOCUMENTS

| | | | | |
|---|---|---|---|---|
| 5,549,621 A | * | 8/1996 | Bessler et al. | 606/151 |
| 5,906,625 A | * | 5/1999 | Bito et al. | 606/142 |
| 5,910,149 A | | 6/1999 | Kuzmak | |
| 6,494,886 B1 | * | 12/2002 | Wilk et al. | 606/142 |
| 6,572,627 B2 | * | 6/2003 | Gabbay | 606/151 |
| 7,635,374 B2 | * | 12/2009 | Monassevitch et al. | 606/142 |
| 2002/0068946 A1 | | 6/2002 | Kortenbach et al. | |
| 2004/0059280 A1 | | 3/2004 | Makower et al. | |
| 2004/0267291 A1 | | 12/2004 | Byrum et al. | |
| 2006/0116679 A1 | | 6/2006 | Lutz et al. | |
| 2006/0161139 A1 | | 7/2006 | Levine et al. | |
| 2006/0264699 A1 | | 11/2006 | Gertner | |
| 2007/0032807 A1 | | 2/2007 | Ortiz et al. | |

OTHER PUBLICATIONS

PCT/US2007/015238; International Searching Authority, PCT Search Report, dated Aug. 27, 2008.
PCT/US2007/015238, International Searching Authority, Written Opinion, dated Aug. 27, 2008.
PCT/US2008/055303, International Searching Authority, PCT Search Report, dated Nov. 18, 2008.
PCT/US2008/055303, International Searching Authority, Written Opinion, dated Nov. 18, 2008.

* cited by examiner

*Primary Examiner* — Darwin Erezo
*Assistant Examiner* — Alexander Orkin
(74) *Attorney, Agent, or Firm* — Ice Miller LLP

(57) ABSTRACT

A device, system and method for providing tissue and organ restriction. Embodiments of an implantable magnetic device are described with respect to restricting gastric capacity while avoiding nutritional deficiencies and other complications. Further, a delivery device is described for facilitating the delivery of the magnetic device to a targeted site. Additionally, methods are described for delivering the magnetic devices to a stomach.

31 Claims, 17 Drawing Sheets

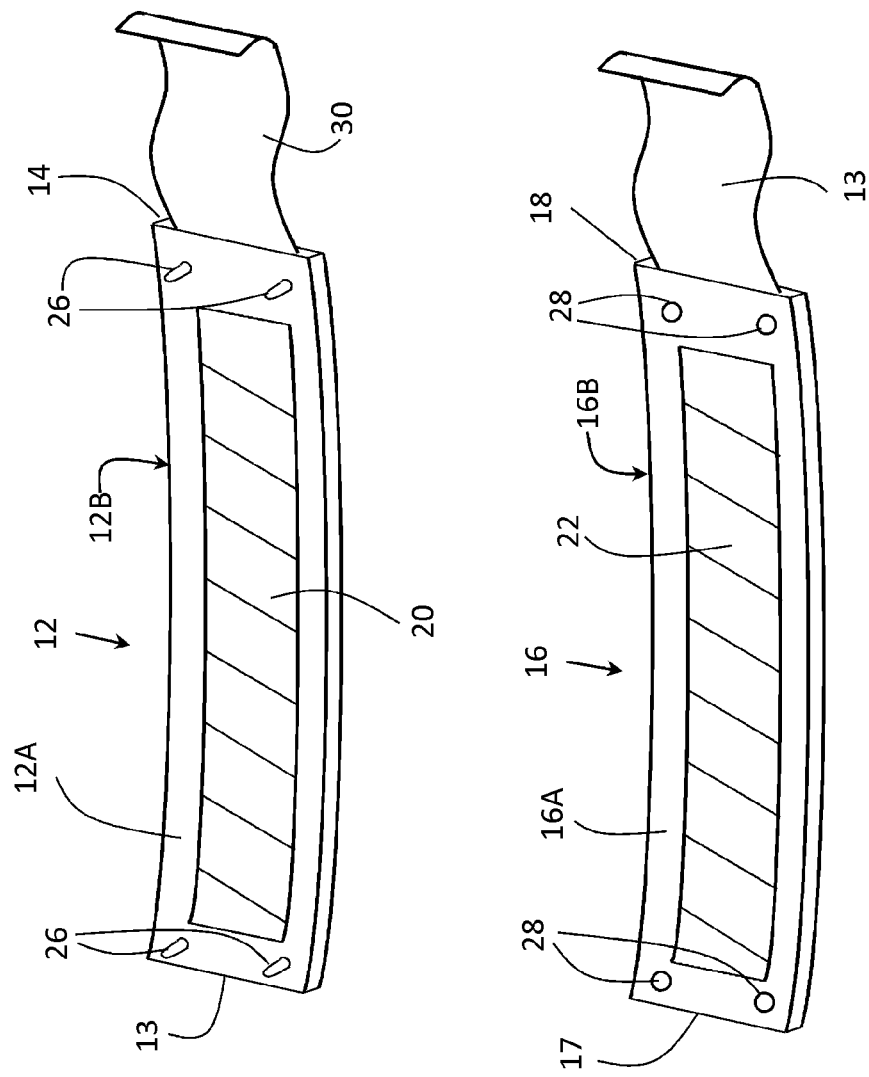

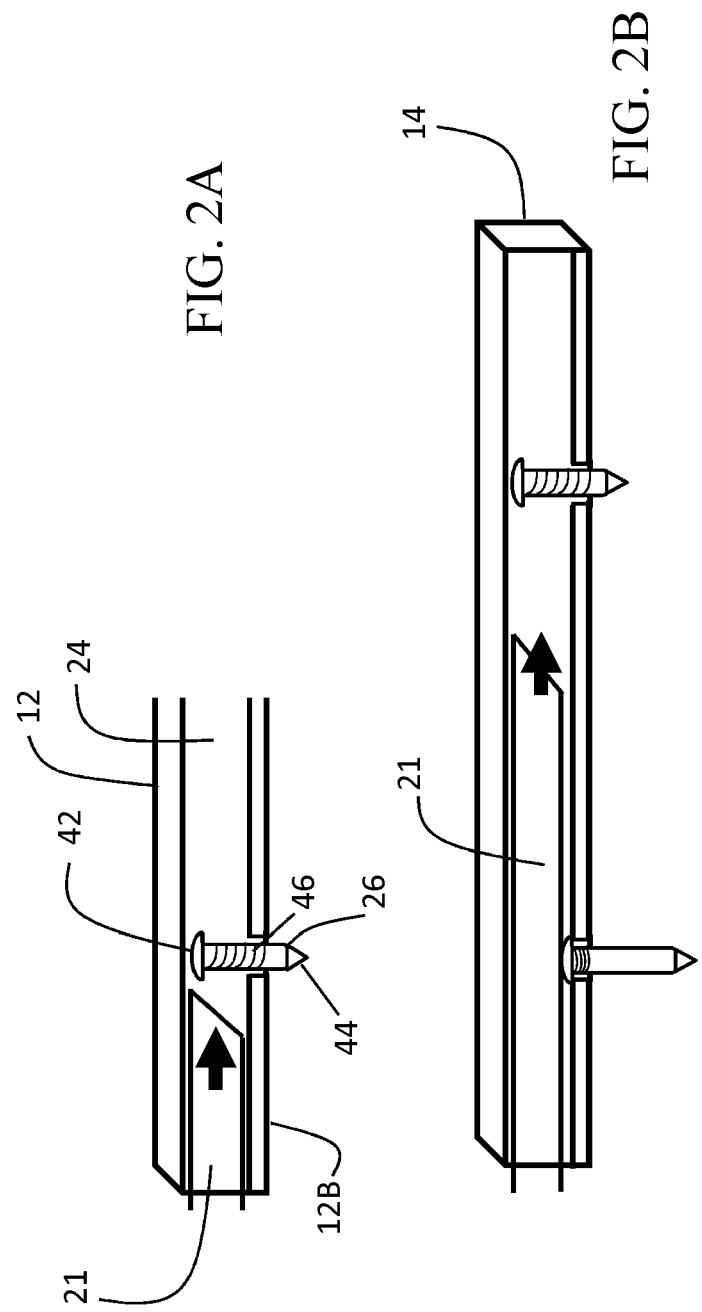

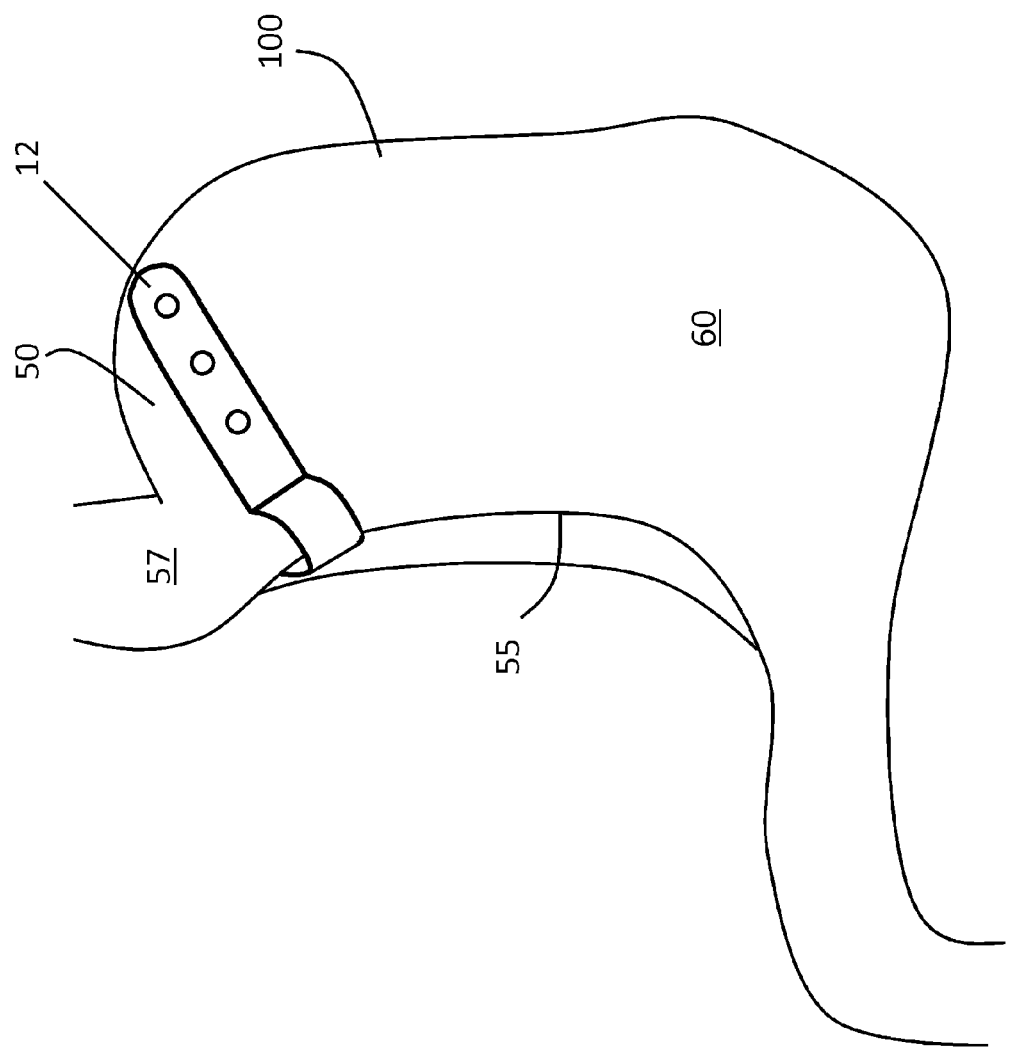

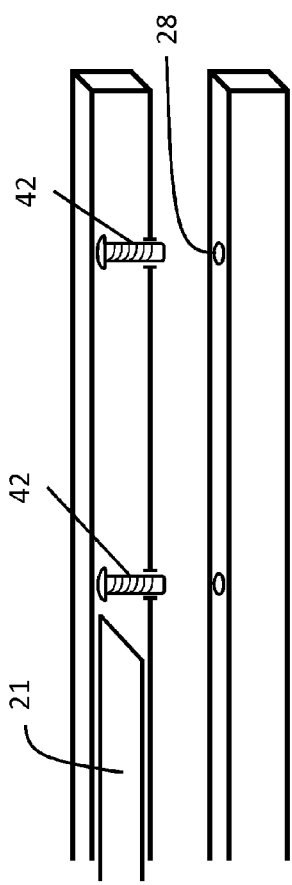
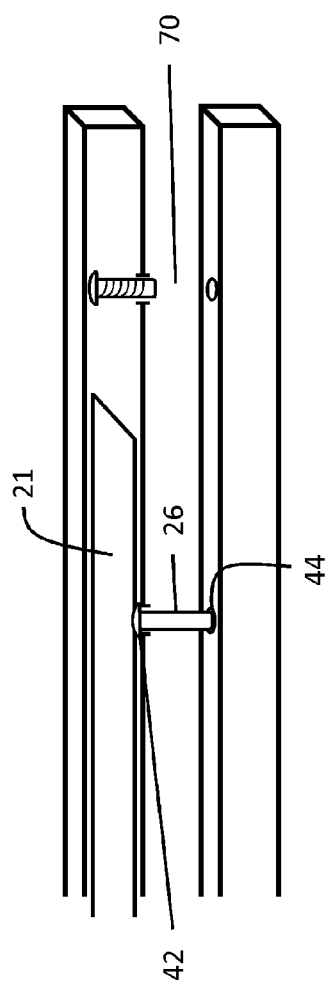
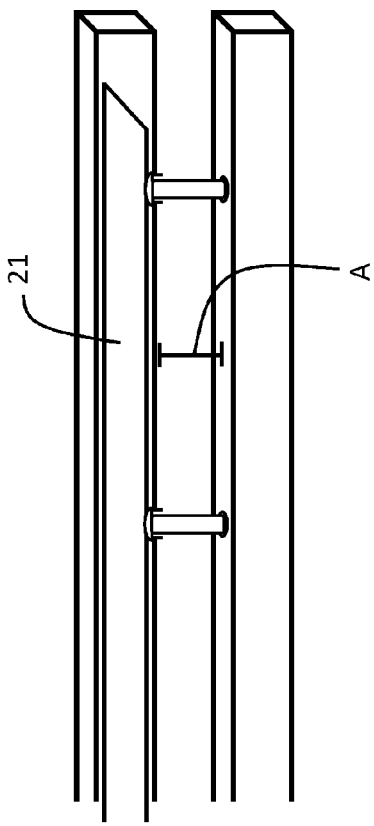
FIG. 4A
FIG. 4B
FIG. 4C

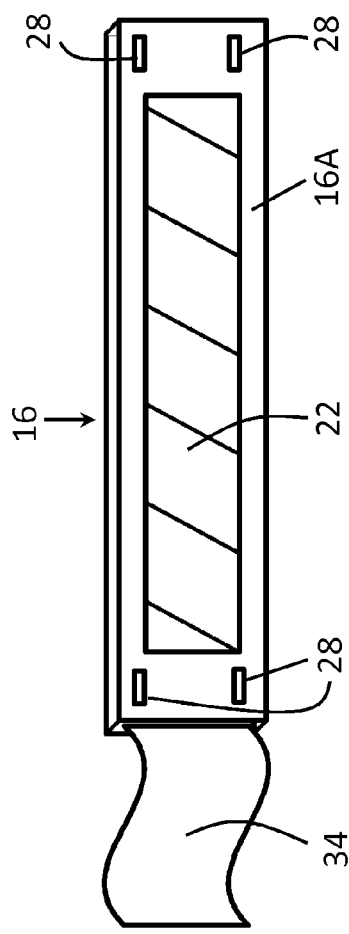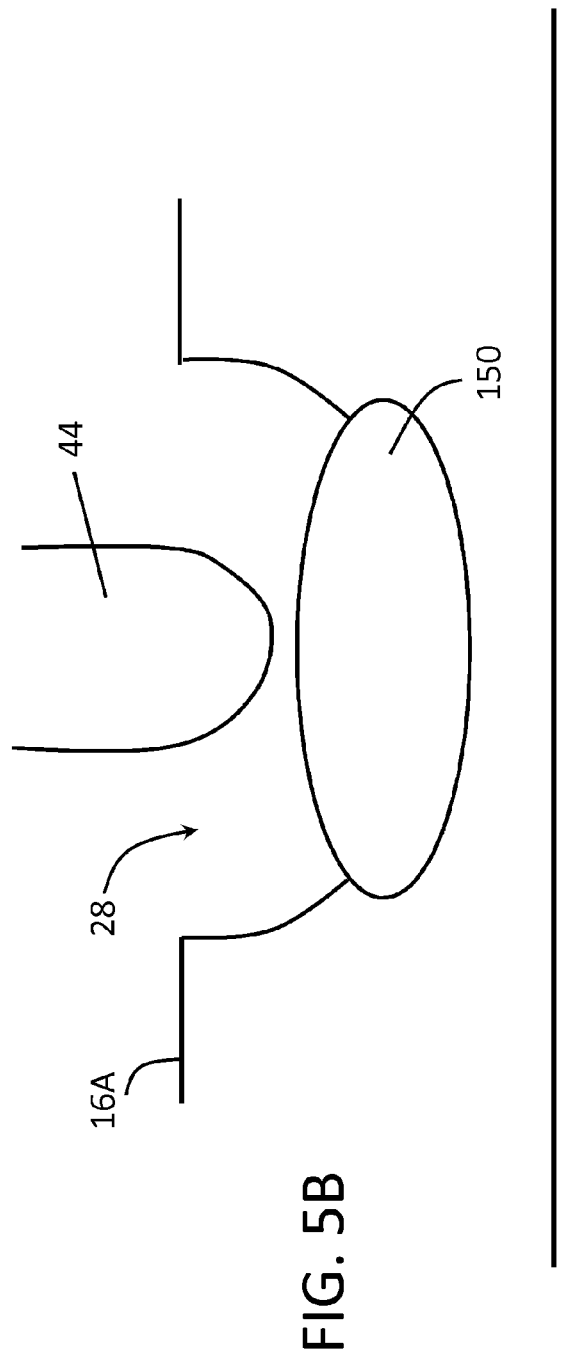

FIG. 6B
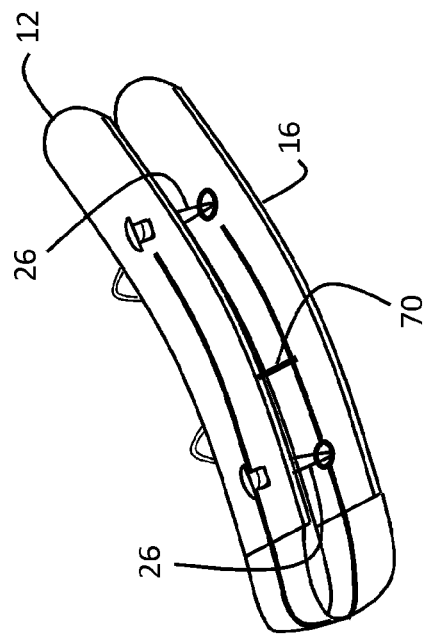
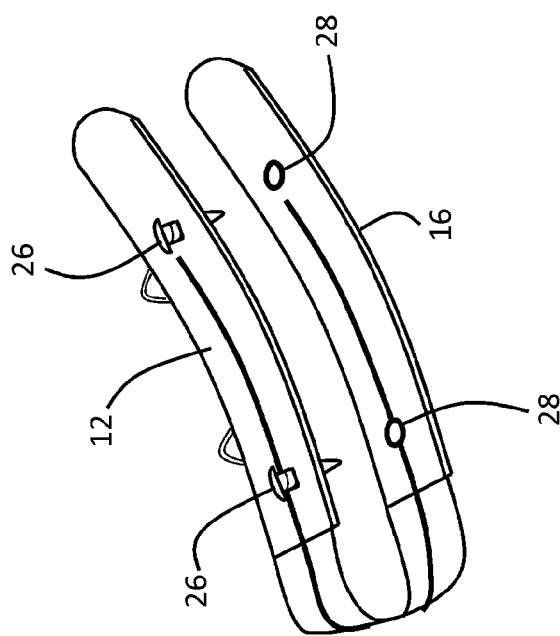

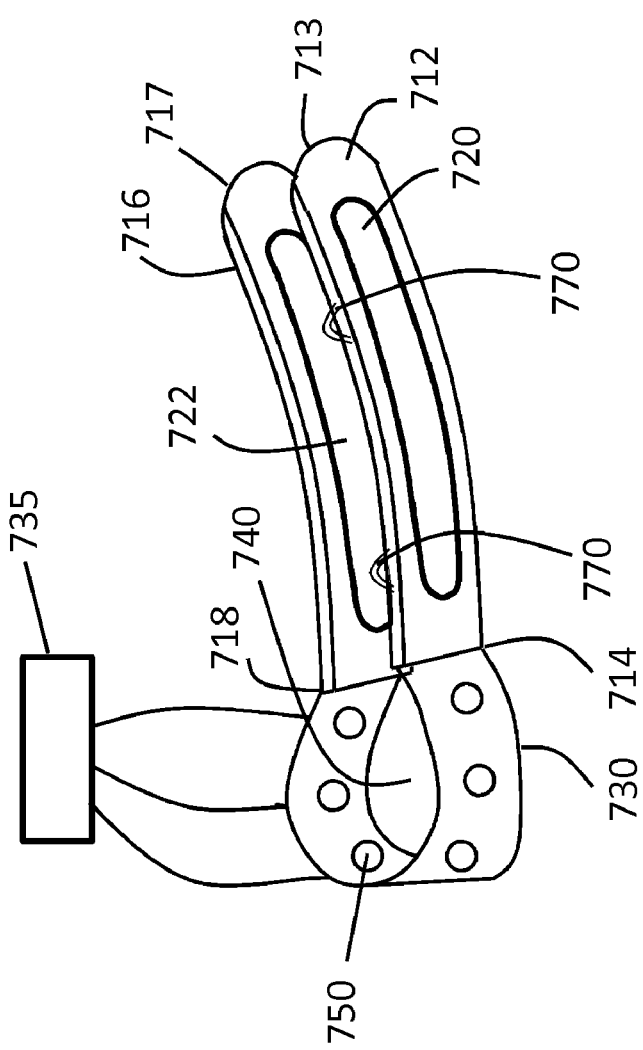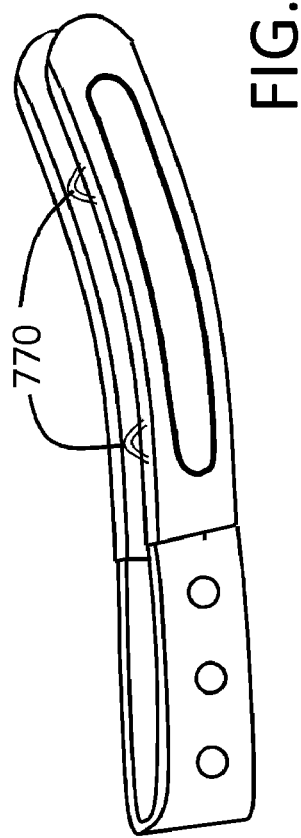
FIG. 7A
FIG. 7B

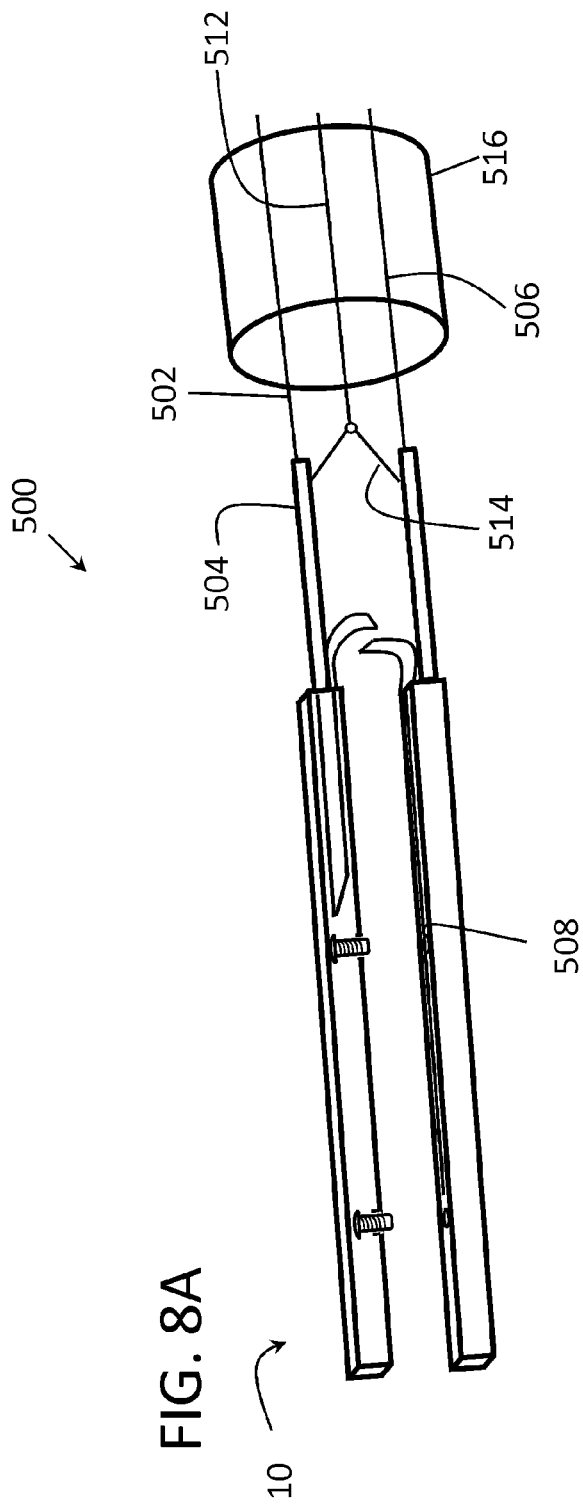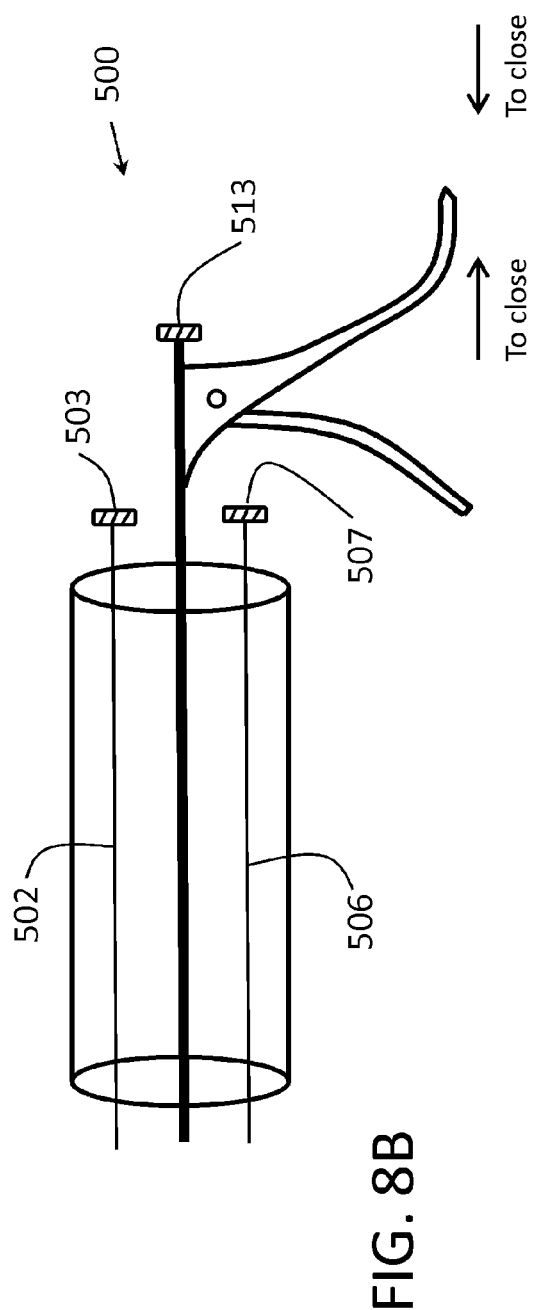
FIG. 8A
FIG. 8B

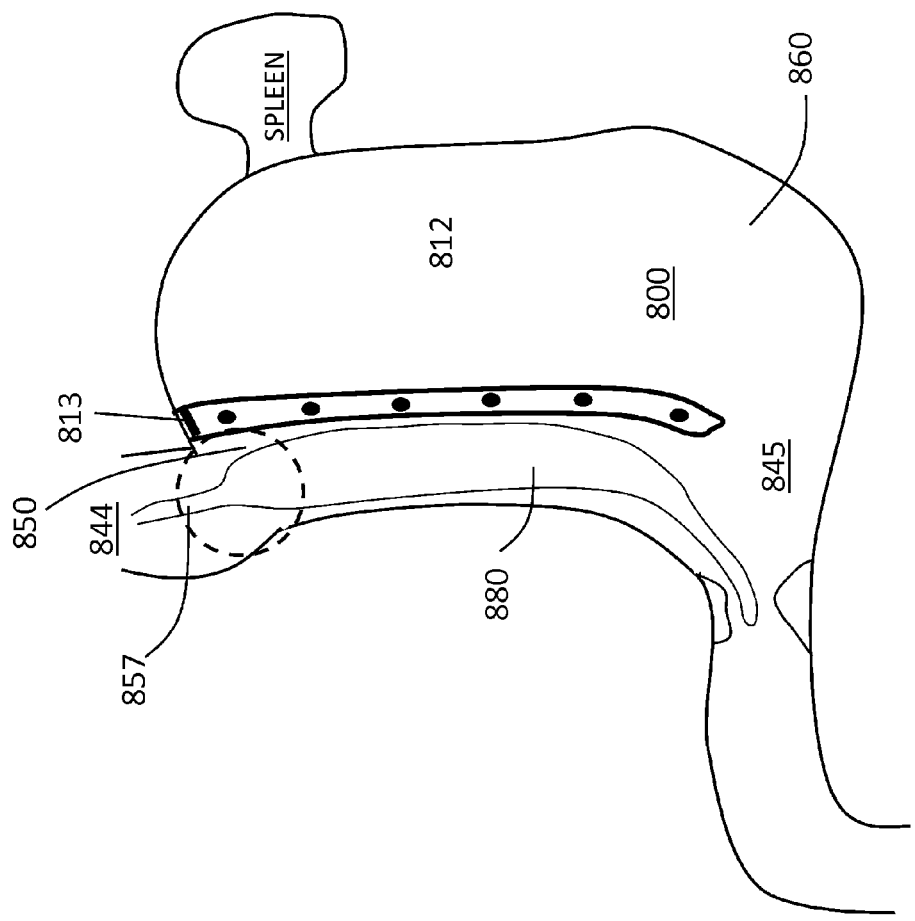

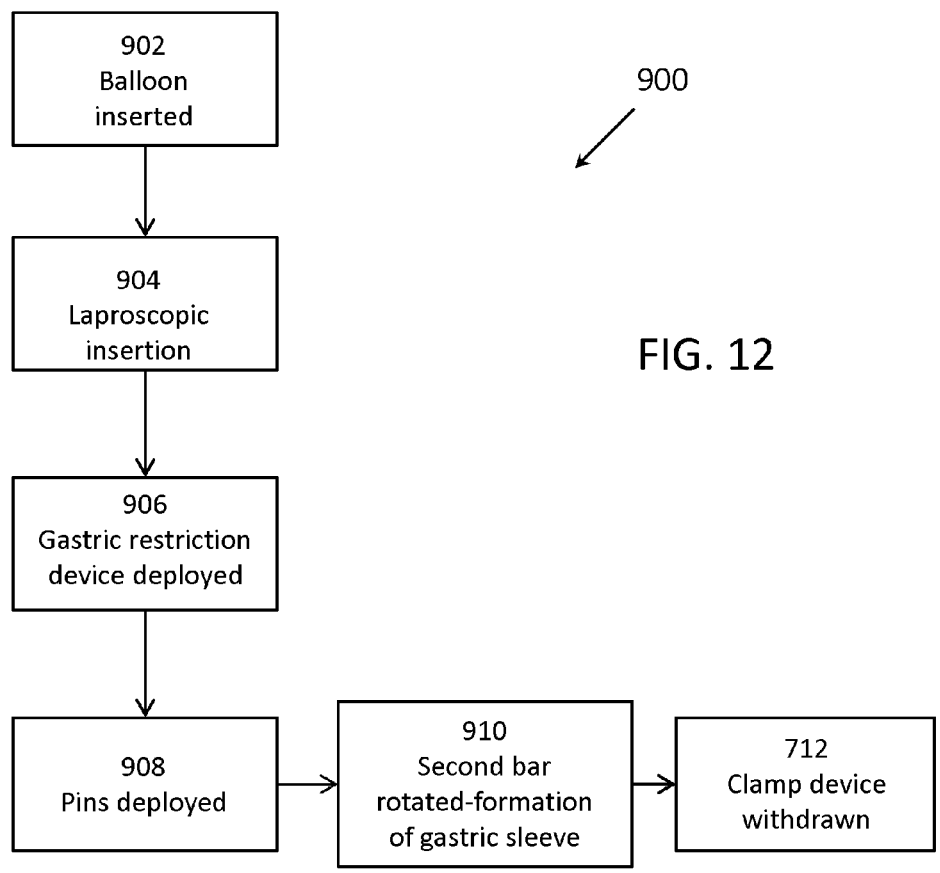

DEVICES, SYSTEMS, AND METHODS FOR ORGAN RESTRICTION

PRIORITY

This United States Patent Application is a U.S. National Application of, and claims the priority benefit to, International Patent Application Serial No. PCT/US2008/055,303, filed Feb. 28, 2008, which (a) is related to and claims the priority benefit of U.S. Provisional Patent Application Ser. No. 60/940,627, filed May 29, 2007; (b) is related to and claims the priority benefit of U.S. Provisional Patent Application Ser. No. 60/940,630, filed May 29, 2007; and (c) is related to and claims the priority benefit of International Patent Application No. PCT/US2007/015,238, filed Jun. 29, 2007, which claims priority to U.S. Provisional Patent Application Ser. No. 60/817,423, filed Jun. 30, 2006. The contents of each of these applications are hereby incorporated by reference in their entirety into this disclosure.

BACKGROUND

Obesity and overweight conditions are a global epidemic and are the most frequent nutritional disorder in Western civilization. Currently, the conditions of "overweight" and "obesity" are classified by body mass index ("BMI"), which is a statistical measure of the weight of a person scaled according to height. From the period of 1988-1994 to the period of 1999-2000, the incidence of overweight adults augmented from 55.9% to 64.5% while the prevalence of obesity increased from 22.9% to 30.5%. The United States especially faces grave public policy concerns with respect to the morbidly obese, i.e. being over 100 pounds above their desirable weight or having one or more serious medical conditions in association with obesity.

In order to treat obesity, conventional procedures involve attempts to either 1) restrict food intake into the body via a restrictive bariatric procedure (a "Restrictive Procedure"), or 2) alter the anatomy of the small intestine or divert the peristalsis of a person's normal food intake past the small intestine to decrease caloric absorption via a malabsorptive bariatric procedure, which is commonly known as a gastric bypass (a "Malabsorptive Procedure"). It is also known to combine the two procedures such that both of the aforementioned techniques are employed jointly.

Each of the abovementioned procedures has advantages and disadvantages. The Malabsorptive Procedures, which entail short circuiting the gastric pouch, have previously been more successful in bringing about sustained weight loss; however, they are typically more difficult to perform, have higher rates of catastrophic post-operative complications, and produce long-term deleterious changes due to the rerouting of the alimentary flow. Restrictive Procedures have encountered more success than Malabsorptive Procedures because the Restrictive Procedures tend to be simpler, have fewer major complications, and do not disturb normal digestive tract continuity.

In Malabsorptive Procedures, an intestinal bypass is typically performed. This results in the exclusion of almost all of the small intestine from the digestive tract, such that a lower amount of calories and nutrients can be absorbed. One example of a specific Malabsorptive Procedure is the biliopancreatic diversion ("BPD"). BPD is a procedure in which about three-fourths (¾) of the stomach is removed in order to restrict food intake and decrease stomach acid production. The effect of this procedure is to alter the anatomy of the small intestine via the formation of an alimentary limb. The alimentary limb diverts the passage of food past the first portion of the small intestine, including the duodenum and jejunum, thereby preventing all of the bile and pancreatic juices from digesting the ingested food. As briefly noted above, this process does not come without significant risks.

Conversely, in Restrictive Procedures a passageway is generally constructed from the upper portion of the stomach to the lower portion, thereby preventing the stomach from storing large amounts of food and slowing the passage of food from the esophagus to the small intestine. Conventional Restrictive Procedures rely on the banding and/or stapling of the stomach to create a small pouch on the superior portion of the stomach near the gastroesophageal junction. When first created, this pouch can contain no more than approximately one (1) ounce of food and liquid, but typically later distends to store two (2) to three (3) ounces.

The lower outlet of the created pouch is nondilatable and is typically only one half (½) inch in diameter or smaller. The small pouch receives food and liquid directly from the esophagus and fills quickly. The pouch also diverts the passage of food and liquid to the lower portion of the stomach, thus avoiding storage of food in the stomach itself. Due to the pouch's size and the relatively narrow outlet into the larger stomach, the patient experiences early satiety, which in turn decreases appetite and results in weight loss. Purely Restrictive Procedures for obesity include adjustable gastric banding and vertical banded gastroplasty. These procedures do not affect the digestive process and thus do not result in the risks associated with Malabsorptive Procedures. In addition, Restrictive Procedures are safer than Malabsorptive Procedures and can be performed laparoscopically, thereby further reducing risks of complications.

In all Restrictive Procedures, the volume of the small pouch above the band can increase in size up to ten (10) times after the initial operation. Therefore, the pouch volume during surgery needs to initially be very small. To enable the patient to consume sufficient nutrition immediately after the operation considering such a small gastric pouch, the opening to the lower portion of the stomach must initially be relatively large. Thereafter, as the pouch volume increases, the opening must be subsequently reduced to enjoy optimal results of the procedure. In addition, the size of the opening should be gradually reduced during the first year after surgery as the gastric pouch increases in size.

One Restrictive Procedure, adjustable gastric binding ("AGB"), provides an adjustment means, thereby enabling minor post-operation adjustments of the size of the opening to the lower portion of the stomach. In AGB, a band is placed around the superior portion of the stomach to form a small pouch and a narrow passageway to the rest of the stomach. The band itself typically comprises a hollow silicone rubber band having an inflatable cavity. The inflatable cavity of the band is capable of being inflated with a fluid—typically an isotonic salt solution—through a tube that connects the band to an access port, which is typically located subcutaneously so that it may be easily accessed by the patient. Over time, the band may be tightened or loosened to modify the size of the opening to the lower portion of the stomach by increasing or decreasing the quantity of fluid within the cavity of the band. By adding liquid to the cavity of the band, the band expands radially inward and decreases the size of the opening to the lower portion of the stomach.

A great disadvantage of AGB, however, is that as a result of the direct manipulation of the bands, the rubber bands forming the gastric pouch tend to slip or wear away. In addition, in the conventional AGB process where the fluid is added to the band cavity by way of an injection into the access port, repeated injections into the same area increases the risk of infection in the area surrounding the access port. In addition, it is uncomfortable for the patient when the necessary post-operation adjustments of the opening are carried out by using a needle to access the port through the skin of the patient.

Similar to AGB, vertical banded gastroplasty ("VBG") is a Restrictive Procedure that utilizes rubber bands as well as staples to create the small stomach pouch. Unlike AGB, however, VBG is not manually adjustable. The VBG procedure involves puncturing the stomach to create a pouch. Like AGB, VBG is prone to slippage and/or band deterioration. Additional complications also may arise with VBG, including staple-line disruption, which can result in stomach content leakage and/or serious infection. Such complications may require prolonged hospitalization with antibiotic treatment and even additional operations. Based on the associated risks, VBG has been classified by the American Medical Association as a "severely dangerous" operation.

Combined operations consisting of Malabsorptive and Restrictive Procedures are the most common bariatric procedures performed today. Such combined procedures restrict both food intake and the amount of calories and nutrients that the body is capable of absorbing. An example of a combined procedure is the Extended (Distal) Roux-en-Y Gastric Bypass ("RYGBP-E") in which a stapling creates a small (approximately 15 to 20 cc) stomach pouch completely separated from the remainder of the stomach. The small intestine is divided just beyond the duodenum (the hollow tube connecting the stomach to the jejunum), and is re-arranged into a Y-configuration to enable outflow of food from the small upper stomach pouch, via a "Roux limb". Accordingly, the small intestine forms the outlet of the newly formed stomach pouch, which empties directly into the lower portion of the jejunum, thus bypassing caloric absorption. The length of either segment of the intestine can be increased to adjust the levels of malabsorption.

Because the duodenum is bypassed in this procedure, poor absorption of iron and calcium can result in a decreased total body iron concentration and a predisposition to iron deficiency anemia. Additional complications of the RYGBP-E procedure include a condition known as "dumping syndrome". Normally, the pyloric valve at the lower end of the stomach regulates the release of food into the bowel. Dumping syndrome is a condition in which the stomach contents rapidly pass into the small intestine resulting in extremely unpleasant conditions including nausea, weakness, sweating, faintness and, on occasion, diarrhea after eating. Because sugar passes especially rapidly into the bowel, some patients are unable to eat any form of sweets after RYGBP-E surgery.

Being obese has many health ramifications. Obesity is an important risk factor for a number of diseases and increases risk factors that heavily predispose for cardiovascular disease. In addition, systemic hypertension, pulmonary hypertension (left ventricular failure, chronic hypoxia), and coronary heart disease all occur with excessively high frequency in obese individuals and may be the source or influence in cardiac structure and function alterations. The risk of sudden cardiac death is also elevated in obese individuals.

Accordingly, a need exists for a safe, reversible, and effective method of treating obesity. The current Restrictive, Malabsorptive, and combination procedures present a high risk of several complications, including malnutrition, infections, vomiting, and recurrence resulting from band slippage or deterioration. There is therefore a need for a new restrictive laparoscopic technique that is reversible and not subject to the complications associated with the conventional procedures known in the art.

SUMMARY

Implantable devices, systems and methods are provided for the treatment of obesity and, specifically, for reversibly restricting the medically effective volume of a stomach. In one embodiment, the device comprises a first bar and a second bar. The first bar comprises a first magnet, a first strap and at least one pin coupled therewith, and the second bar comprises a second magnet and a second strap. In this at least one embodiment, the first magnet of the first bar and the second magnet of the second bar are magnetically biased to attract and engage a portion of the stomach therebetween. However, the pins of the first magnet provide an amount of space between the first magnet and the second magnet so that the tissue disposed therebetween is not overly compressed. In application of the implantable device to a stomach divides the stomach into a first portion and a second portion. Further, the first and second straps are disposed adjacent to or around the lesser curvature of the stomach and form an outflow tract such that the first portion of the stomach is in communication with the second portion. The first portion of the stomach is for the primary digestion of ingested food, while the second portion of the stomach is largely bypassed in the digestive process.

In additional embodiments, the second bar comprises a plurality of receptacles for receiving the pins of the first bar. These receptacles may be elongated in shape or comprise a mechanism to allow for the lateral movement of the pins when received therein. In this manner, the receptacles can prevent shearing of the tissue pinned therebetween. Still further, the pins may be fixed or moveable between a retracted position and an extended position.

In still other embodiments, the first and second straps of the gastric restriction device may comprise the same strap or may be disposed on the stomach adjacent to each other but not in physical connection. The first and second straps may comprise a hook-and-loop fastener system, a buckle system, or any other fastening system. In addition, the first and second straps may be comprised of a membrane lace material, including, without limitation, polyurethane, polytetrafluoroethene, and silastic. Further, the first and second straps may comprise a plurality of electromagnetic sensors coupled with a subcutaneous power source. When activated, these electromagnetic sensors are capable of decreasing the size of the outflow tract formed between the straps by pulling the first and second straps closer to each other.

In still other embodiments, the first and second bars can be comprised of a corrosion resistant material such as, and without limitation, polyurethane, polytetrafluoroethylene, silastic, and titanium. Further, the first bar may comprise a channel extending therethrough and a shaft configured to be slidably inserted into the channel. In this embodiment, the shaft is slidably moved through the channel to deploy the pins and thereby move the pins from the retracted position to the extended position. Similarly, a resistance mechanism may be coupled with each pin to bias each of the pins in the retracted position such that the pins remain in the retracted position until the shaft is slidably moved through the channel.

Various embodiments of a delivery device for laparoscopically delivering the above-described embodiments of the gastric restriction device to a stomach are also provided. In at least one embodiment, the delivery device comprises a first arm, a second arm, a lift system, and a hollow casing. In this embodiment, both the first and second arms are configured to releasably couple with individual components of the gastric restriction device. Further, in one embodiment, the first arm and the second arm are both capable of rotational movement. In yet another embodiment, only the second arm is capable of rotational movement. The lift system comprises an activation mechanism, a first branch coupled with the first arm of the delivery device, and a second branch coupled with the second arm of the delivery device. The hollow casing comprises an elongated tube having a hollow interior extending therethrough and is capable of laparoscopic introduction into a body. In one embodiment, each of these components may be manipulated to slidably deliver and coordinate the components of the gastric restriction device.

In application, the various above-described embodiments of the gastric restriction device and delivery device may be used to reversibly achieve a reduced medically effective size of a stomach. In at least one embodiment, a method is provided for delivering the gastric restriction device to the stomach. In one embodiment, the first bar and the second bar of the gastric restriction device are coupled with the first arm and the second arm of the delivery device, respectively, and disposed within the interior of the hollow casing. The casing is advanced laparoscopically into a patient's abdominal cavity. In one embodiment, the first bar and the second bar of the gastric restriction device are advanced out of the interior of the hollow casing and positioned adjacent to the stomach. In certain embodiments, the gastric restriction device can be applied to the stomach in an axial or longitudinal fashion such that a gastric sleeve is formed extending from the gastroesophageal junction to the pre-pyloric area without interfering with the pyloric sphincter. In other embodiments, the gastric restriction device is applied to the stomach transversally to form a small pouch such that the medically effective portion of the stomach is located proximal to the gastroesophageal junction and an opening allows digested food matter to flow into the residual portion of the stomach. In certain embodiment, the size of the opening can be regulated by the first and second straps of the gastric restriction device to achieve the desired weight loss and/or appetite suppression results. In each of these embodiments, the pins of the first bar prevent the physical interaction of the first and second bars and thereby prevents the over compression of the stomach tissue therebetween.

In one embodiment, when the first bar and the second bar are disposed within the interior of the hollow casing, the second bar is rotated in a fashion opposing its magnetic polarity such that the first bar and the second bar do not magnetically engage one another. This embodiment facilitates the delivery of the first and second bars to the exterior walls of the stomach as a clinician does not have to overcome a magnetic bond between the first and second bars prior to deploying the bars on a stomach. Once the gastric restriction device has been delivered to the stomach and is in the desired position, the first and second arms can be disconnected from the first and second bars, respectively, and the delivery device is withdrawn. In one embodiment, the first and second arms are unscrewed from the first and second bars of the gastric restriction device. In other embodiments, other fastening mechanisms are employed.

BRIEF DESCRIPTION OF THE DRAWINGS

FIGS. 1A and 1B show side views of at least one embodiment of the components of a gastric restriction device;

FIGS. 2A and 2B show side, cross-sectional views of the components of FIGS. 1A and 1B;

FIG. 3A shows a side view of the gastric restriction device of FIGS. 1A-2B positioned on a stomach;

FIGS. 4A, 4B, and 4C show cross-sectional views of at least one embodiment of a gastric restriction device;

FIG. 5A shows a side view of at least one embodiment of a second bar of a gastric restriction device having at least one embodiment of multiple receptacles disposed therein;

FIG. 5B shows a side view of the receptacle of FIG. 5A;

FIG. 6B shows a perspective view of an additional embodiment of a fastening mechanism of a gastric restriction device;

FIGS. 7A and 7B show an open and closed view, respectively, of an alternative embodiment of a gastric restriction device;

FIGS. 8A, 8B, and 8C show cross-sectional views of at least one embodiment of a clamp device coupled with the gastric restriction device of FIGS. 1A-2B;

FIG. 11B shows the gastric restriction device of FIG. 11A applied to a stomach in such a manner so as to create a gastric sleeve; and FIG. 12 shows a flow chart of a method for delivering the gastric restriction device of FIGS. 11A-11B to a stomach using a clamp device and a balloon.

DETAILED DESCRIPTION

Figure 1B:
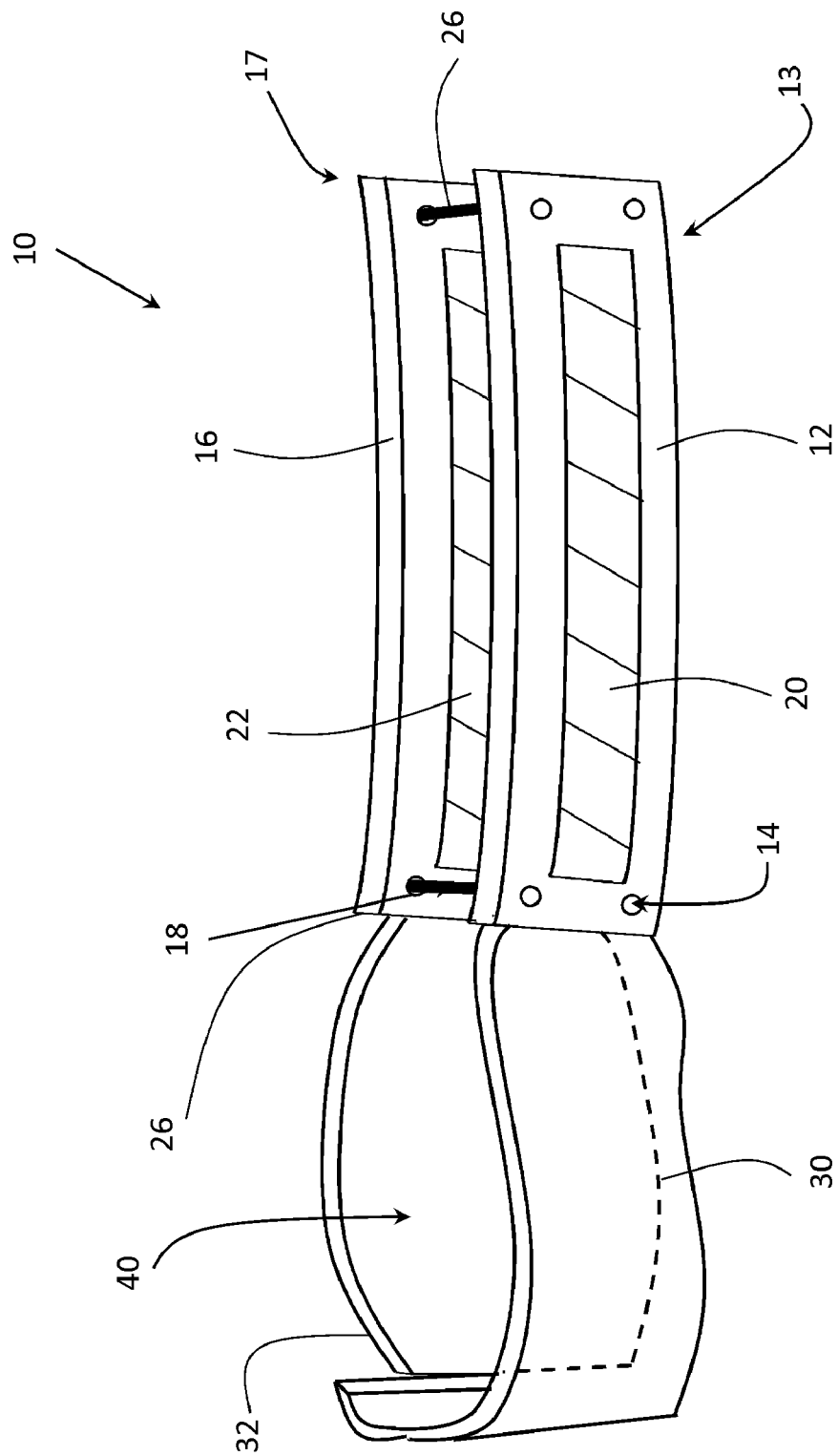

Reference will now be made to the embodiments illustrated in the drawings and specific language will be used to describe the same. It will nevertheless be understood that no limitation of scope is intended by the description of these embodiments.

FIGS. 1A, 1B, 2A, and 2B show at least one embodiment of a gastric restriction device 10. In this embodiment, the gastric restriction device 10 comprises an implantable device and avoids the nutritional deficiencies observed with Malabsorptive Procedures, does not require sutures or staples that could lead to dehiscence (e.g., the opening of the suture site), fistula (e.g., an abnormal connection between organs or intestines), or a significant amount of regurgitation and vomiting, and is reversible. The gastric restriction device 10 is configured to be positioned on the anterior and posterior walls of a stomach following the gastric vascular irrigation (see FIG. 3). The gastric restriction device 10 functions to form a small gastric pouch for receiving food through the gastroesophageal junction and prevent distension by applying pressure to the anterior and posterior walls of the stomach. A portion of the gastric restriction device 10 is also positioned around the lesser curvature of the stomach, allowing for the regulation of the size of the outflow tract of the pouch.

In the embodiment shown in FIGS. 1A and 1B, the gastric restriction device 10 comprises a first bar 12 and a second bar 16. The first bar comprises a proximal end 13, a distal end 14, a body having a first side 12A and a second side 12B, and a first strap 30 extending from the distal end. In one embodiment, the first bar 12 further comprises a channel 24 extending through the body from the proximal end 13 to the distal end 14 that houses at least two pins 26 (see FIGS. 2A and 2B). The first side 12A of the first bar 12 is configured to be positioned on the anterior wall of a stomach. The second bar 16 comprises a proximal end 17, a distal end 18, and a body having a first side 16A and a second side 16B. The second bar 16 may further comprise at least two receptacles 28 positioned on the first side 16A in such a manner that the receptacles 28 correspond with the positioning of the at least two pins 26 of the first bar 12. The second side 16A of the second bar 16 is configured to be positioned on the posterior wall of a stomach. Each of the bars 12, 16 may be configured in a straight or curved configuration. For example, in at least one embodiment, the first and second bars 12, 16 of FIG. 1A comprise a slightly curved configuration similar to the anterior and posterior walls of a stomach.

The body of the first bar 12 further comprises a first magnet 20 and the body of the second bar 16 further comprises a second magnet 22. For example, in at least one embodiment, the bodies of the first and second bars 12, 16 comprise thin, smooth ferromagnetic bars. In an alternative embodiment shown in FIGS. 1A and 1B, the bodies of the first and second bars 12, 16 comprise a material suitable to resist corrosion, such as and without limitation, polyurethane, polytetrafluoroethylene ("PTFE"), silastic, titanium, or any other material suitable use in the medical arts that is corrosion resistant. In this embodiment, the first and second magnets 20, 22 are either encased within the non-corrosive material or disposed thereon along the first sides 12A, 16A, respectively.

It will be appreciated that each magnet 20, 22 may comprise the totality of the first or second bar 12, 16, or be disposed within or on the first or second bar 12, 16 in any fashion so long as an attractive magnetic force can be generated between the first side 12A of the first bar 12 and the first side 16A of the second bar 16. In other words, the first bar 12 is configured such that the portion of the magnet 20 positioned along the first side 12A of the first bar 12 comprises a polarity that is opposite of, and therefore attractive to, the polarity of the portion of the second magnet 22 positioned along the first side 16A of the second bar 16. As shown in FIG. 3, when the first side 12A of the first bar 12 is positioned against the anterior wall of a stomach 100 and the first side 16A of the second bar 16 is positioned against the posterior wall of the stomach 100, the magnets 20, 22 are biased to compress the stomach 100 therebetween and create a first stomach pouch 50 and a second residual stomach portion 60. Further, the magnets 20, 22 can be positioned on the first and second bars 12, 16 in such a manner that a clinician can easily align the bars 12, 16 when delivering the gastric restriction device 10 laparoscopically.

Further, due to general magnetic principles (i.e. the two different ends of a magnet exhibit opposite polarities), the portion of the magnets 20, 22 positioned adjacent to the second sides 12B, 16B of the first and second bars 12, 16 necessarily comprises a polarity opposite that of the polarity exhibited by the same magnet 20, 22 adjacent to the respective first side 12A, 16A. In this manner, the portion of the second magnet 22 positioned adjacent to or along the second side 16B of the second bar 16 comprises the same polarity as the portion of the magnet 20 positioned along the first side 12A of the first bar 12. Because like polarities create a repellant force when disposed adjacent to one another, when the second side 16B of the second bar 16 is positioned adjacent to the first side 12A of the first bar 12 the two magnetic portions of like polarities repel each other. This repellent force can be exploited during the delivery of the gastric restriction device 10 to a stomach, as will be described in further detail herein.

Now referring back to FIGS. 2A and 2B, the first bar 12 further comprises a channel 24 extending the length thereof, a shaft 21 that is slidably moveable within the channel 24, at least two moveable pins 26 positioned within the channel 24, and at least two openings 46 disposed through the first side 12A. The channel 24 communicates with the proximal end 13 of the first bar 12 such that the shaft 21 may be advanced and retracted through the channel 24 through the proximal end 13 of the first bar 12. In this embodiment, the channel 24 has a depth substantially equal to or greater than the length of the moveable pins 26 and is configured such that a device may be slidably moved therethrough.

In at least one embodiment, the pins 26 are movable and disposed within the channel 24 of the first bar 12 perpendicular to the longitudinal axis of the channel 24. In each of the locations where a pin 26 is positioned within the channel 24 an opening 46 is disposed through the first side 12A of the first bar 12 such that the pin 26 can be extended therethrough (see FIG. 2A). Alternatively, in another embodiment, the pins 26 are fixed such that the pins 26 permanently extend from the first side 12A.

Each of the pins 26 comprises a rigid material such as a metal, a plastic, or any other material suitable for use in the medical arts. Further, each of the pins 26 comprises a proximal end 42 and a distal end 44, and may comprise any length as long as the pins 26 are of a sufficient size to move through a laparoscopic port. In one embodiment, the pins 26 are about 7 to about 16 millimeters long. It will be understood that a clinician can select the length of the pins 26 based on the thickness of the stomach that is to be treated.

The proximal end 42 and the distal end 44 may be configured similarly or differently, in either a blunt or tapered configuration. In at least one embodiment, the pins 26 are metallic, the proximal end 42 comprises a blunt configuration, and the distal end 44 comprises a tapered configuration. In an alternative embodiment, the distal end 44 of each of the pins 26 may comprise a blunt configuration. In yet another embodiment, the proximal ends 42 of the pins 26 are configured to have larger diameters than those of the openings 46 such that the proximal ends 42 of the pins 26 are prevented from moving through the openings 46 and disengaging from the first bar 12. It will be appreciated that any number of pins 26 may be employed. In the embodiments shown in FIGS. 1A and 1B, the first bar 12 comprises four pins 26; two pins 26 coupled with the proximal end 13 and two pins 26 coupled with the distal end 14.

In the at least one embodiment where the pins 26 are movable, each of the pins 26 is capable of moving between a retracted position and an extended position. Further, each of the pins 26 can move independently of the other pins 26 such that one or more of the pins 26 may be in the retracted position while one or more of the pins 26 are in the extended position. When a pin 26 is in the retracted position, the pin 26 is disposed within the channel 24 of the first bar 12 such that the pin 26 extends across the width of the channel 24. Depending on the length of the pin 26, the distal end 44 of the pin 26 may or may not protrude through the corresponding opening 46 in the first side 12A of the first bar 12. In one embodiment, the pins 26 are shorter in length and do not extend past the first side 12A until the pins 26 are moved into the extended position.

As shown in FIG. 2B, when the shaft 21 is advanced through the channel 24 such that a force is applied to the proximal ends 42 of the pins 26, the pins 26 move from the retracted position to the extended position. In one embodiment, the proximal end of the shaft 21 is configured in a pointed configuration to facilitate the application of downward pressure to the proximal ends 42 of the pins 26 when the shaft 21 is advanced thereover. As a pin 26 moves into the extended position, the distal end 44 of the pin 26 advances through its respective opening 46 and past the first side 12A of the first bar 12.

When the pressure is removed from the distal end 42 of the pin 26 (i.e. the shaft 21 is withdrawn from the channel 24), the pin 26 slidably moves back into the retracted position. Thus, the pin 26 is biased to be positioned in the retracted position. In one embodiment, a resistance mechanism 48 is coupled with each of the pins 26 to provide this bias. In the embodiment shown in FIGS. 2A and 2B, the resistance mechanism 48 comprises a spring system, wherein a spring 48 is coiled around each of the pins 26. As seen in FIG. 2A, when the pin 26 is positioned in the retracted position, the spring 48 is expanded and stores little, if any, potential energy. However, when the pin 26 is moved to the extended position, the spring 48 is compressed and thus stores potential energy (see FIG. 2B). In this manner, the spring 48 provides enough resistance that the pin 26 remains in the retracted position when no pressure is applied. It will be appreciated that any type of resistance mechanism can be employed that is capable of providing resistance to the pins 26 when they are moved to the extended position.

When the first side 12A of the first bar 12 is magnetically engaged with the first side 16A of the second bar 16, the at least two movable pins 26 are used to maintain the first bar 12 at a target distance away from the second bar 16. As shown in FIGS. 4A-4C, the pins 26 are positioned in the extended position and the distal ends 44 of the pins 26 couple with the first side 16A of the second bar 16. In this manner, the pins 26 oppose the magnetic force exerted between the first magnet 20 and the second magnet 22 and prevent the first bar 12 from contacting the second bar 16. Furthermore, an interior space 70 is defined between the first bar 12 and the second bar 16 and has a depth similar to the length of the pins 26. The diameter of the interior space 70 can be manipulated by the clinician depending on the thickness of the stomach to be treated or other factors. For example, to achieve an interior space 70 with a larger diameter, the length of the pins 26 may be increased and/or the thickness of the first and second bars 12, 16 may be adjusted.

To prevent the distal ends 44 of the pins 26 from sliding relative to the first side 16A of the second bar 16, in one embodiment, the first side 16A comprises at least two receptacles 28. As shown in FIGS. 4A-4C, the positioning of the receptacles 28 in the first side 16A of the second bar 16 corresponds with the placement of the at least two pins 26 on the first bar 12. In the at least one embodiment where the first bar 12 comprises two pins 26 on the proximal end 13 and two pins 26 on the distal end 14, the first side 16A of the second bar 16 comprises two receptacles 28 on the proximal end 17, corresponding with the pins 26 on the proximal end 13 of the first bar 12, and two receptacles 28 on the distal end 18, corresponding with the pins 26 on the distal end 14 of the first bar 12. It will be recognized that any number of receptacles 28 may be disposed in the first side 16A of the second bar 16. Furthermore, the receptacles 28 may be configured in any manner so long as each receptacle 28 is capable of receiving the distal end 44 of a pin 26 therein. For example, and without limitation, each of the receptacles 28 may be configured to be an indentation, a closed ended hole, a through hole, or any configuration suitable for receiving a particular embodiment of the distal end 44 of a pin 26.

By receiving the distal ends 44 of the pins 26 when the first bar 20 is magnetically engaged with the second bar 16, the receptacles 28 facilitate the secure attachment of the pins 26 with the second bar 16 and prevent the pins 26 from sliding or shearing off of the first side 16A. This is especially advantageous when the gastric restriction device 10 is applied to a stomach 100, as the gastric restriction device 10 can remain properly positioned despite the inherent movement of the normally functioning stomach 100.

One alternative embodiment of the receptacles 28 is shown in FIGS. 5A and 5B. In this embodiment, the receptacles 28 of the second bar 16 further comprise a mechanism 150 to allow for lateral movement of the distal end 44 of a pin 26 received within the receptacle 28. The mechanism 150 may comprise any mechanism capable of facilitating the lateral movement of the distal end 44 of a pin 26 within the receptacle 28. In the embodiment shown in FIGS. 5A and 5B, the mechanism 150 comprises a rotating metallic ball disposed within the bottom portion of the receptacle 28. Further, in this embodiment the receptacle 28 is configured in an elongated shape to allow for movement of the distal end 44 of a pin 26 when the distal end 44 is engaged with the receptacle 28. When this embodiment of the gastric restriction device 10 is applied to a functioning stomach, the mechanism 150 allows the first bar 12 and the second bar 16 to shift relative to each other to accommodate the inherent movement of the stomach, and thereby preventing the shearing of the tissue engaged therebetween.

Referring back to FIGS. 1A and 1B, the proximal ends 14, 18 of the first bar 12 and the second bars 16 are coupled with a first strap 30 and a second strap 34, respectively. The first and second straps 30, 34 comprise a membrane lace material, such as polyurethane, PTFE, silastic, or any other material suitable in the medical arts. The first strap 30 and the second strap 34 are configured such that when the first and second bars 12, 16 are positioned on the anterior and posterior portions of the stomach, the first strap 30 and the second strap 34 are disposed proximate to or around the lesser curvature of the stomach. Further, the first and second strap 30, 34 are configured to define an interior space 40 therebetween when the first and second bars 12, 16 are disposed in this manner (see FIG. 1B). The first and second straps 30, 34 may comprise any degree of flexibility or rigidity and may comprise any or no fastening mechanism so long as when the first bar 12 and the second bar 16 are employed on a stomach 100, the interior space 40 is formed between the first strap 30 and the second strap 32.

Figure 6A:
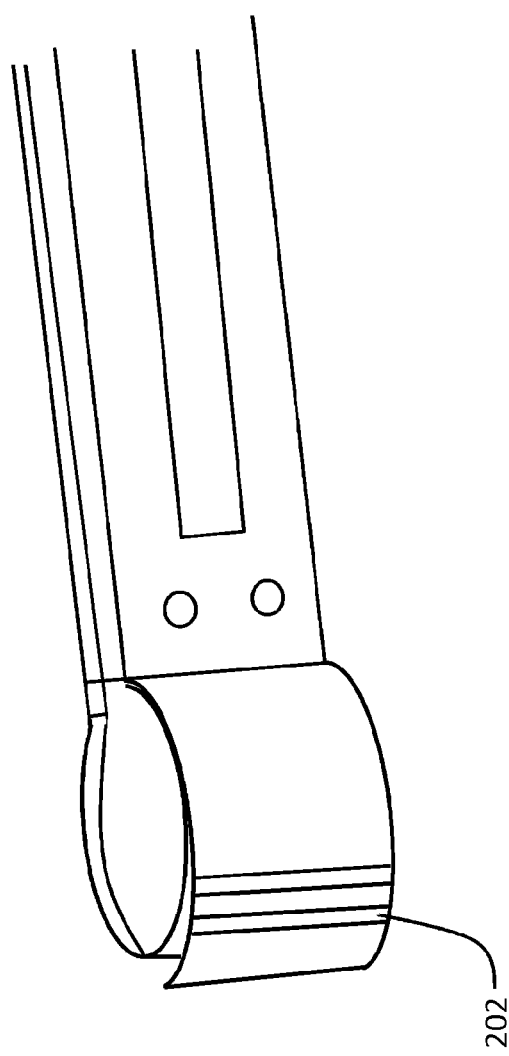
FIG. 6A shows a perspective view of at least one embodiment of a fastening mechanism of a gastric restriction device.

Depending on the configuration of the first and second straps 30, 34, the first and second straps 30, 34 may fasten together around the lesser curvature of the stomach. In at least one alternative embodiment, the first and second straps 30, 34 do not physically fasten together, yet still cause the interior space 40 to be maintained. In this embodiment, the first and second straps 30, 34 may comprise a rigid material capable of maintaining a shape without additional support. In an alternative embodiment, the first strap 30 and the second strap 34 comprise a fabric hook-and-loop fastener system such as Velcro®. For example, the first strap 30 may comprise a "hook" side comprising a plurality of small plastic hooks, and the second strap 34 may comprise a "loop" side comprising a plurality of small plastic loops. Accordingly, when the first and second straps 30, 34 fasten together around the lesser curvature of the stomach, the hooks of the first strap 30 catch the loops of the second strap 34 which thereby releasably fastens the two straps 30, 34 together. In an additional embodiment shown in FIG. 6A, the first and second straps 30, 34 may fasten together through use of a buckle system. In this embodiment, the buckle system comprises a clasp 202 coupled with the second strap 34 for retaining the end of the first strap 30. In yet another embodiment, the first and second straps 30, 34 may be permanently joined together such that the straps 30, 34 comprise a single element (membrane lace 35) as shown in FIG. 6B. In this embodiment, the membrane lace 35 is rigid to provide an outflow limitation as discussed in more detail below.

Figure 3B:
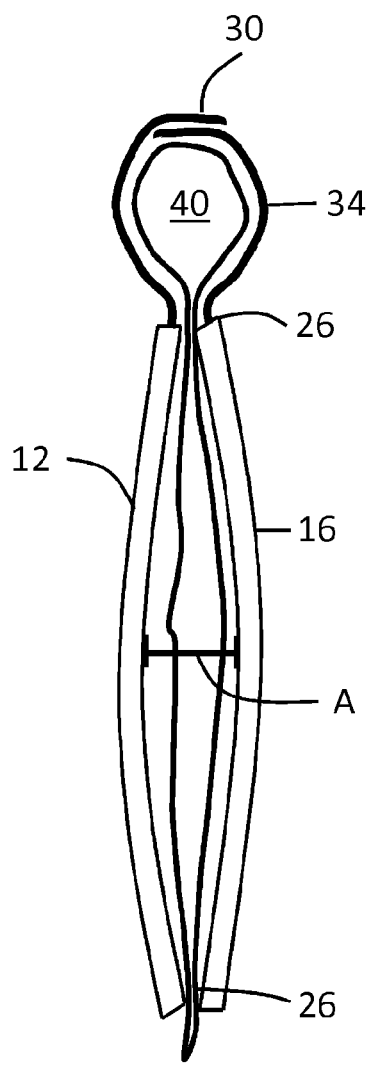
FIG. 3B shows a top, cross-sectional view of the gastric restriction device of FIGS. 1A-2B positioned on a stomach.

Referring now to FIG. 3B, when the gastric restriction device 10 is used to treat a stomach 100, the interior space 40 forms the outflow tract of the gastric pouch 50 created by the gastric restriction device 10. Accordingly, the diameter of the outflow tract of the gastric pouch 50 can be adjusted in a number of ways, including without limitation: modification of the length of the first and second straps 30, 34; the degree of overlap between the first and second straps 30, 34 around the lesser curvature of the stomach; and the degree of expansion available in the material comprising the first and second straps 30, 34. A clinician may modify such variables to achieve the precise diameter and/or size of the gastric outflow tract.

In operation and as previously discussed, in one embodiment, the gastric restriction device 10 is applied to a stomach 100 as shown in FIG. 3A. Specifically, the first side 12A of the first bar 12 is positioned adjacent to the anterior wall of the stomach 100 and the first side 16A of the second bar 16 is positioned adjacent to the posterior wall of the stomach 100, such that the first and second straps 30, 34 of the gastric restriction device 10 is positioned proximate adjacent to the lesser curvature 55 of the stomach 100 proximal to the gastroesophageal junction 57 (the "GEJ 57"). Due to the placement of the first and second bars 12, 16 the first side 12A of the first bar 12 is magnetically engaged through the stomach tissue with the first side 16A of the second bar 16, thereby encasing the stomach walls therebetween. As illustrated in FIG. 3B, when the gastric restriction device 10 is deployed, the at least two pins 26 of the first bar 12 maintain the first bar 12 at a target distance A from the second bar 16. In this embodiment, the at least two pins 26 are the only portion of the gastric restriction device 10 that directly engage the underlying stomach 100. Accordingly, the at least two pins 26 prevent the gastric restriction device 10 from overly compressing the tissue. The pins 26 pock the anterior gastric walls and assume the majority of the compressional force, as opposed to the underlying tissue.

Accordingly, when the first bar 12 and the second bar 14 are positioned on the stomach 100 and magnetically engaged, the stomach 100 is divided into two portions—one small gastric pouch 50 and one larger, residual stomach portion 60. Due to the size of the small gastric pouch 50, the amount of food that the patient can consume at one time is significantly reduced and satiety is more quickly achieved. Further, the outflow tract defined by the interior space 40 formed by the first and second straps 30, 34 of the gastric restriction device allows food matter received through the GEJ 57 to move into the residual gastric pouch in a controlled manner, such that the food matter can proceed through normal digestion. While the delineation between the small gastric pouch 50 and the residual gastric pouch is not leak-proof, the magnetic force between the first and second bars 12, 16 provides support to the anterior and posterior stomach walls such that the stomach 100 is prevented from distending. In this manner, most of the food matter received into the small gastric pouch 50 through the GEJ 57 is maintained therein and the patient exhibits the sensation of satiety earlier.

Now referring to FIGS. 7A and 7B, an additional embodiment of a gastric restriction device is shown. A gastric restriction device 700 comprises a first bar 712, a second bar 716, a membrane lace 730, and a power supply 735. The first bar 712 comprises a proximal end 713 and a distal end 714, and the second bar 716 comprises a proximal end 717 and a distal end 718. Similar to the configuration of the first and second bars 12, 16 of the gastric restriction device 10, the first bar 712 of the gastric restriction device 700 comprises a first magnet 720 and the second bar 716 of the gastric restriction device 700 comprises a second magnet 722. In one embodiment, the first and second magnets 720, 722 each comprise a permanent magnet. Further, in at least one embodiment, both the first and second bars 712, 716 comprise at least one stitch loop 770 extending therefrom. The at least one stitch loop 770 may comprise any configuration so long as the stitch loop 770 is capable of coupling with sutures to assist in securing the gastric restriction device 700 to the stomach.

The membrane lace 730 is coupled with the distal end 714 of the first bar 712 and the distal end 718 of the second bar 716. In this manner, the membrane lace 730 forms a closed loop comprising an interior space 740. When the gastric restriction device 700 is applied to a stomach to create a small gastric pouch, the interior space 740 defines an outlet from the small gastric pouch so that an outflow of digested matter can flow to therethrough into the lower portion of the stomach. Accordingly, the size of the interior space 740 affects how quickly food and other digested matter may exit the small gastric pouch.

In one embodiment, a plurality of electromagnetic sensors 750 are disposed along the surface of the membrane lace 730 and function to adjust the size of the interior space 740. Each of the electromagnetic sensors 750 is coupled with the power supply 735 that is implanted subcutaneously on the patient. The power supply 735 is capable of supplying a current that activates the electromagnetic sensors 750. Upon activation, the electromagnetic sensors 750 are magnetized and attract one another, thereby decreasing the circumference of the membrane lace 730 and, thus, decreasing the size of the interior space 740.

Accordingly, application of the gastric restriction devices 10, 700 achieves a small gastric pouch 50 while avoiding constriction and excessive compression of the gastric walls. Further, when the membrane lace 730 comprises electromagnetic sensors 750, the size of the interior space 740 is easily adjustable in a noninvasive manner. Remodeling of the tissue is avoided, which prevents adhesions from developing in the underlying stomach 100 and allows for the complete reversal of the procedure. Further, because the normal process of digestion is not altered, malabsorption syndromes and metabolic deficiencies are avoided. Due to the relatively simple delivery of the devices 10, 700, the gastric restriction devices 10, 700 may be used in conjunction with other techniques, or as a bridge to decrease the body mass index of a patient prior to undergoing a radical surgical procedure (e.g., gastric bypass).

Using the gastric restriction devices 10, 700 described herein in the treatment of obesity avoids the nutritional deficiencies observed after Malabsorptive Procedures, does not require sutures or staples which may lead to dehiscence or fistula formation, or produce the degree of regurgitation and vomiting observed in connection with conventional methods used to treat obesity. Moreover, each of the embodiments described herein may be inserted into the body cavity laparoscopically, thereby decreasing the stress associated with the procedure and the patient's recovery time. It will be recognized by one of skill in the art that any of the devices described herein may be employed in combination with the other conventional bariatric procedures.

Figure 8C:
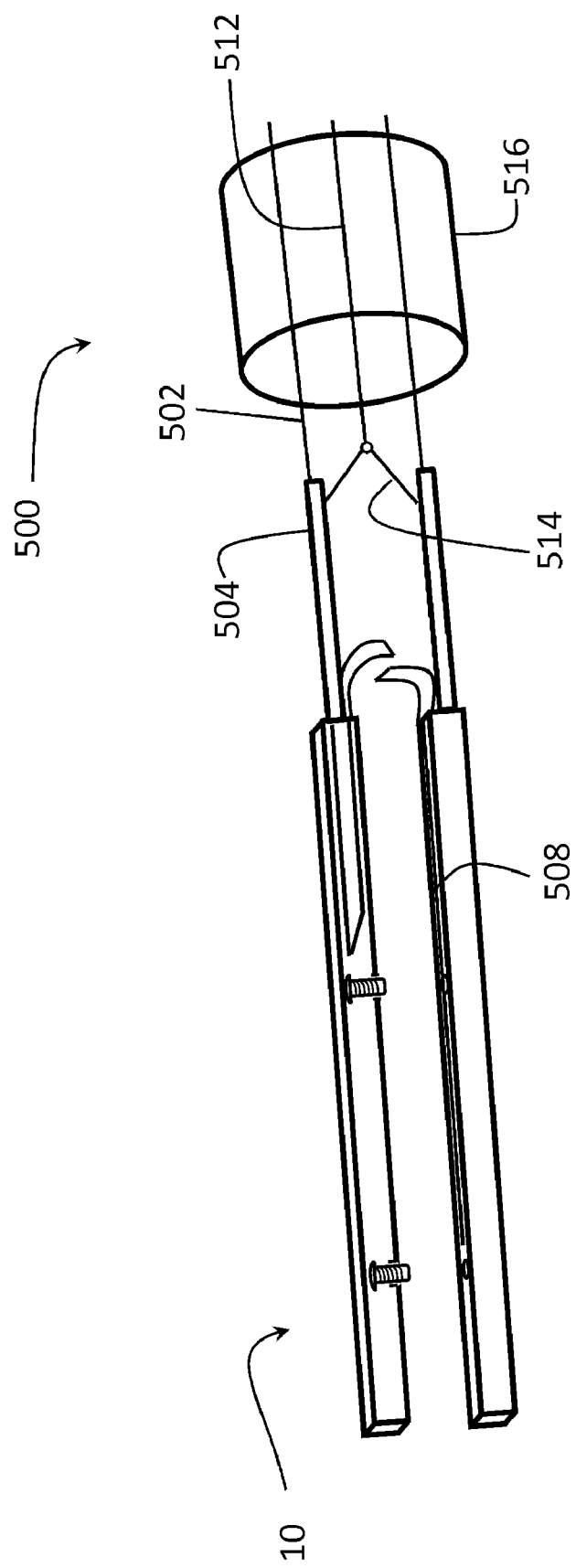

Now referring to FIGS. 8A, 8B, and 8C, one embodiment of a clamp device 500 is shown. The clamp device 500 may be used to deliver the gastric restriction device 10 to the stomach 100 laparoscopically and comprises a first arm 502, a second arm 506 and a lift system 512. Each of the first arm 502, the second arm 506 and the lift system 512 are slidably disposed within a hollow casing 516 configured for laparoscopic delivery. In one embodiment, the hollow casing 516 comprises a distal end for advancement through the body of a patient, and the distal end is open such that the first arm 502, the second arm 506 and the lift system 512 may be delivered therethrough once properly positioned within the body.

The first arm 502 has a proximal end 503 and a distal end 504 and may comprise any rigid material capable of advancing the shaft 21 of the gastric restriction device 10 through the channel 24. In at least one embodiment, the first arm 502 is capable of rotational movement. The second arm 506 similarly has a proximal end 507 and a distal end 508 and may comprise any rigid material such as a metal. The second arm 506 is further capable of rotational movement and the distal end 508 thereof may be configured in a screw-like configuration. It will be appreciated that the first arm 502 and the second arm 506 are independent of each other such that a clinician can advance the distal end 504 of the first arm 502 independently of the second arm 506 (and vice versa).

Figure 9:
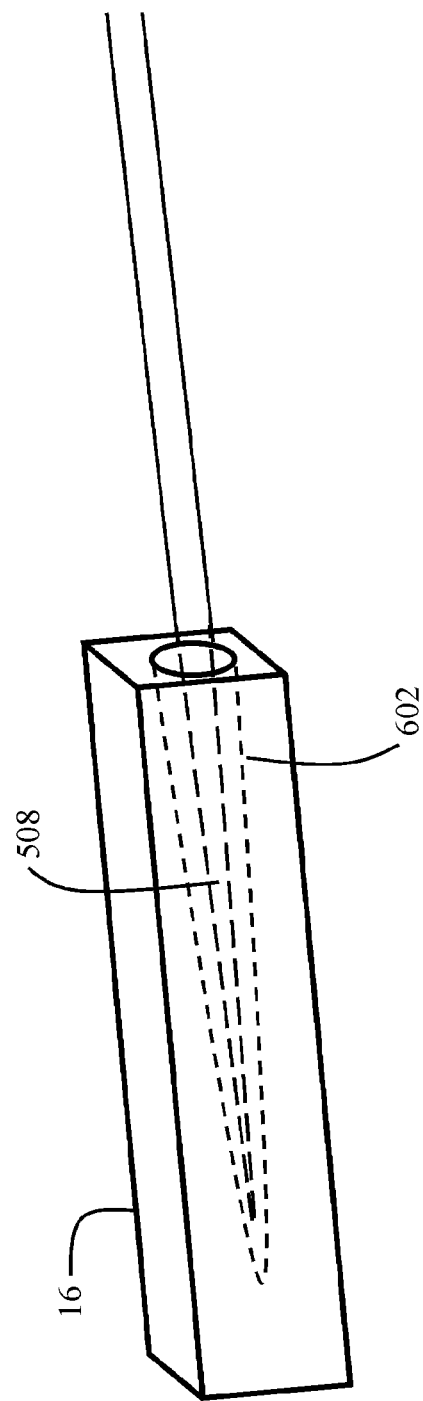
FIG. 9 shows a perspective view of one embodiment of a second bar of a gastric restriction device.

When the clamp device 500 is employed to deliver the gastric restriction device 10 to a stomach 100, the distal ends 504, 508 of the first and second arms 502, 504 are removably coupled with the gastric restriction device 10. Specifically, the distal end 504 of the first arm 502 is removably coupled with the shaft 21 of the first bar 12 and the distal end 508 of the second arm 506 is removably coupled with the second bar 16. In one embodiment shown in FIG. 9, the second bar 16 comprises a hollow interior space 602 configured to receive the distal end 508 of the second arm 504 of the clamp device 500. In the embodiment shown in FIG. 9, the distal end 508 of the second arm 506 comprises a screw-tip configuration and the hollow interior space 602 of the second bar 16 is configured to rotatably mate therewith.

Due to the magnetic attraction between the first and second bars 12, 16 of the gastric restriction device 10, when the magnetic components of the gastric restriction device 10 are positioned in close proximity with each other within the hollow casing 516, it is often desired to prevent the components from magnetically engaging until the device 10 is delivered to the stomach 100. The clamp device 500 can prevent any undesired magnetic interaction through the use of the rotatable second arm 506.

As previously described with respect to the configuration of the gastric restriction device 10, the first side 12A of the first bar 12 and the second side 16B of the second bar 16 comprise like polarities and the first side 16A of the second bar 16 and the second side 12B of the first bar 12 comprise like polarities. Accordingly, in one embodiment, when the gastric restriction device 10 is positioned within the hollow casing 516 the second arm 506 coupled with the second bar 16 may be rotated to position the second side 16B of the second bar 16 adjacent to the first side 12A of the first bar 12. As like polarities generate a repellant force, the two bars 12, 16 repel one another and are easily and independently maneuverable within the hollow casing 516.

The lift system 512 of the clamp device 500 may be any device capable of moving the first bar 12 and the second bar 14 relative to each other during the laparoscopic delivery of the gastric restriction device 10. In one embodiment, the lift system 512 comprises a proximal end 513 comprising a hand grip and a distal end 514 comprising a Y-shaped configuration. In this embodiment, the Y-shaped configuration of the distal end 514 comprises a first branch coupled with the distal end 504 of the first arm 502 and a second branch is coupled with the distal end 508 of the second arm 506. The branches of the distal end 514 of the lift system 512 are configured such that when no pressure is applied to the hand grip of the proximal end 513, the branches are positioned in an open configuration such that the first and second arms 502, 506 are spaced a distance apart. Likewise, when pressure is applied to the hand grip of the proximal end (i.e. the hand grip is squeezed), the branches of the distal end 514 of the lift system 512 are pulled proximally such that the branches are moved into a closed configuration and the first and second arms 502, 506 are pulled together within the hollow casing 516.

When the clamp device 500 is used to deliver the gastric restriction device 10 and the first and second arms 502, 506 are coupled with the first and second bars 12, 16 as previously described, moving the branches of the lift system 512 from the open configuration to the closed configuration effectively moves the first and second bars 12, 16 relative to each other. For example, when the branches of the distal end 514 of the lift system 512 are in the open configuration, the first bar 12 and the second bar 16 are positioned a distance apart. However, when the branches of the distal end 514 are moved to the closed configuration, the first bar 12 and the second bar 16 are brought together. In this manner, the clamp device 500 can be used to position the first and second bars 12, 16 of the gastric restriction device 10 on the desired location of the anterior and posterior walls of a stomach 100.

Figure 10:
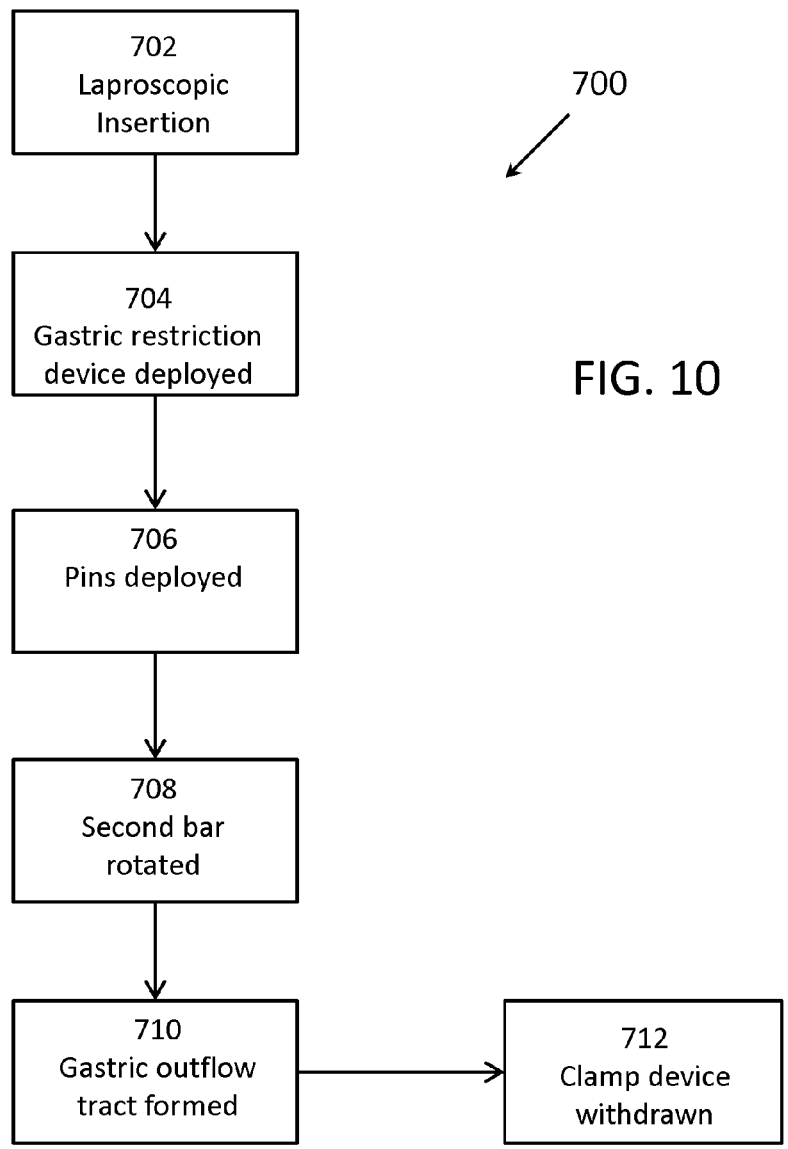
FIG. 10 shows a flow chart of a method for delivering the gastric restriction device of FIG. 8 to a stomach using a clamp device.

Now referring to FIG. 10, a flow chart of a method 700 for laparoscopically delivering the gastric restriction device 10 is shown. While the method 700 is described with respect to the gastric restriction device 10 and the clamp device 500, it will be appreciated that various other devices may be used to achieve the laparoscopic delivery such as a camera and a device for delivering a gas to the abdomen.

At step 702, the distal end of the hollow casing 516 is advanced laparoscopically into a patient's abdomen. Under fluoroscopic or direct camera control, the distal end of the hollow casing 516 is positioned proximate to the stomach 100. As previously described, while the gastric restriction device 10 is positioned within the hollow casing 516, the first side 12A of the first bar 12 and the second side 16B of the second bar 16 are positioned adjacent to one another such that the magnets 20, 22 of each bar 12, 16 repel each other. At step 704, once the distal end of the hollow casing 516 is properly positioned within the abdominal cavity, the first and second arms 502, 506 are advanced through the hollow casing 516, thereby moving the gastric restriction device 10 through the distal end of the hollow casing 516 and into the abdominal cavity. Accordingly, the first side 12A of the first bar 12 is positioned adjacent to the posterior wall of the stomach 100 and the second side 16B of the second bar 16 is positioned adjacent to the anterior wall of the stomach 100.

After the bars 12, 16 are sufficiently positioned relative to the stomach 100, the pins 26 of the first bar 12 are moved to the extended position at step 706. In one embodiment, at step 706, the pins 26 are extended by advancing the first arm 502 of the clamp device 500 distally, which thereby slidably moves the shaft 21 through the channel 24. In this manner, the shaft 21 applies downward pressure to the proximal ends 42 of the pins 26, which causes the pins 26 to move to the extended position. In at least one embodiment, after the shaft 21 has deployed the pins 26, the shaft 21 may be secured within the channel 24 by a locking mechanism (not shown) such that the pins 26 remain in the extended position. The locking mechanism may comprise a latching mechanism, a clip, a fastener, or any other mechanism that is capable of retaining the shaft 21 within the channel 24. In another embodiment, the dimensions of the shaft 21 can be manipulated to affect how far the pins 26 extend from the first side 12A of the first bar 12. For example and without limitation, the depth of the shaft 21 can be configured to be less than the depth of the channel 24 such that when the shaft 21 is used to move the pins 26 into the extended position, the pins 26 do not fully extend through the openings 46 and the springs 48 are not fully compressed. It will be appreciated that step 706 may occur prior to step 704 such that the pins 26 of the first bar 12 are deployed prior to advancing the first and second arms 502, 506 through the hollow casing 516 and into the abdominal cavity. Further, in the embodiment wherein the gastric restriction device 10 comprises pins 26 that are fixed in the extended position, step 706 may be omitted from the method 700 altogether.

After the pins 26 are positioned in the extended position, the method 700 advances to step 708. At step 708, the small gastric pouch 50 and the residual gastric pouch 60 are formed. Specifically, the second arm 506 is rotated 180° such that the first side 16A of the second bar 16 is positioned adjacent to the anterior wall of the stomach 100. Accordingly, as the first side 16A of the second bar 16 comprises an opposite polarity of the first side 12A of the first bar 12, an attractive magnetic force is created, thereby causing the first bar 12 and the second bar 16 to move together and create the two pouches 50, 60. The pins 26 extending from the first side 12A of the first bar 12 couple with the first side 16A of the second bar 16 through the stomach tissue and thus create pocks in the posterior wall of the stomach 100. In this manner, the pins 26 bear much of the load of the compression and maintain an interior area 70 between the bars 12, 16, within which the stomach resides.

At step 710, the first and second straps 30, 34 are positioned on the stomach 100 to create the gastric outflow tract 40. In one embodiment, the straps 30, 34 are joined together around the lesser curvature 55 of the stomach 100 using any of the fastening mechanisms described herein. After the gastric restriction device 10 is properly positioned on the stomach 100, the clamp device 500 can be withdrawn at step 712. Specifically, at step 712, the first arm 502 and the second arm 506 are detached from the shaft 21 of the first bar 12 and the second bar 16, respectively. In the embodiment where the second bar 16 further comprises a hollow interior space 602, the second arm 506 is detached from the second bar 16 by rotating the second arm 506 and unscrewing the distal end 508 from the hollow interior space 602.

Figure 11A:
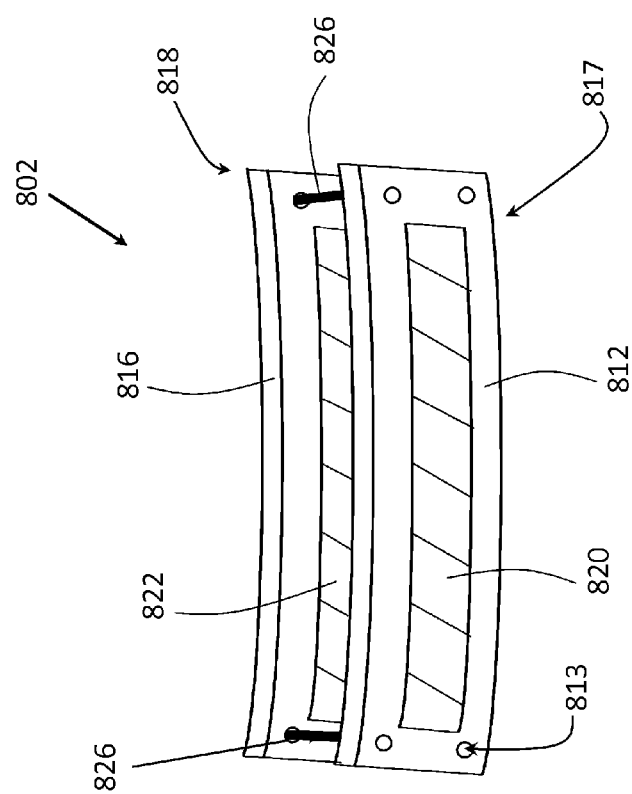
FIG. 11A shows an alternative embodiment of the gastric restriction device of FIGS. 1A-2B.

Now referring to FIGS. 11A and 11B, an alternative embodiment of the gastric restriction device 10 is shown. In this embodiment, the gastric restriction device 802 is comprised identically to the gastric restriction device 10, except that the gastric restriction device 802 may not comprise first and second straps 30, 34. Accordingly, the gastric restriction device 802 comprises a first bar 812 having a proximal end 813, a distal end 814, a first side 812A, a second side 812B, a first magnet 820, at least two pins 826, a channel 824 extending the length thereof, a shaft 821 that is slidably movable within the channel 824, and at least two openings 846 disposed through the first side 812A. The gastric restriction device 802 further comprises a second bar 816 having a proximal end 817, a distal end 818, a first side 816A, a second side 816B, a second magnet 822, and at least two receptacles 828 in the first side 816A. Similar to the at least two receptacles 28 of the gastric restriction device 10, each receptacle 828 is configured to receive at least one of the pins 826 of the first bar 812. As the gastric restriction device 802 is configured similarly to the gastric restriction device 10 that has previously been described in detail, it will be understood that any of the previous-described embodiments disclosed herein can apply to the gastric restriction device 802.

The gastric restriction device 802 may be applied to the stomach 800 as shown in FIG. 11B. In this embodiment, the first side 812A of the first bar 812 is positioned adjacent to the anterior wall of the stomach 800 such that the proximal end 813 is proximate to the GEJ 857, and the second bar 816 is positioned adjacent to the posterior wall of the stomach 800 such that the proximal end 817 is proximate to the GEJ 857. Due to the placement of the first and second bars, 812, 816, the first side 812A of the first bar 812 is magnetically engaged through the stomach tissue with the first side 816A of the second bar 816, thereby encasing the stomach walls therebetween. The restriction of the stomach 800 in this manner forms a gastric sleeve 850 extending from the esophagus 844 to the pre-pyloric area 845, and a residual gastric pouch 860. Accordingly, in at least one embodiment, the first and second bars 812, 816 of the gastric restriction device 802 are capable of spanning from adjacent to the superior surface of the stomach 800 to the inferior surface of the stomach 800. The gastric sleeve 850 comprises an inlet at the GEJ 857 and an outlet at the pre-pyloric area 845, which are the customary entrance for food and fluid entering the stomach 800 and the customary exit for digested food and fluid leaving the stomach 800, respectively. Therefore, even with the gastric remodeling device 802 restricting the stomach 802 in this manner, food digestion can occur through the normal digestive process, thereby avoiding any interruption in the absorption of vitamins and electrolytes typically resulting from Malabsorptive Procedures.

Using the gastric restriction device 802 described herein in the treatment of obesity avoids the nutritional deficiencies observed after Malabsorptive Procedures, does not require sutures or staples which may lead to dehiscence or fistula formation, or produce the degree of regurgitation and vomiting observed in connection with conventional methods used to treat obesity. Moreover, the gastric restriction device 802 may be inserted into the body cavity laparoscopically, thereby decreasing the stress associated with the procedure and the patient's recovery time. It will be recognized by one of skill in the art that any of the devices described herein may be employed in combination with the other conventional bariatric procedures.

Now referring to FIG. 12, a flow chart of a method 900 for laparoscopically delivering the gastric restriction device 802 is shown. While the method 900 is described with respect to the gastric restriction device 802, the previously-described clamp device 500, and a balloon 880, it will be appreciated that various other devices may be used to achieve the laparoscopic delivery such as a camera and a device for delivering a gas to the abdomen.

In one embodiment, the gastric restriction device 800 is used in conjunction with a balloon 880 to form the gastric sleeve 850. The balloon 880 can be any mannequin balloon known in the art as long as the balloon 880 can be introduced endoscopically and the volume of the balloon 880 can be modified when the balloon 880 is positioned within a stomach. When used in conjunction with the gastric restriction device 802, the balloon 880 serves as a model for the desired volume of the gastric sleeve 850. In other words, the balloon 880 provides a reference point for the clinician with respect to the desired size of the effective volume of the stomach, thereby facilitating accurate placement of the gastric restriction device 802 and increasing the overall speed of the procedure. While the application of the gastric restriction device 802 is described in conjunction with a balloon 880 to facilitate the proper sizing of the effective volume, it will be appreciated that the gastric restriction device 802 can be delivered to the stomach 800 without the use of the balloon 880 or other modeling device. Furthermore, the gastric restriction device 802 can be used in conjunction with any other modeling device known in the art, so long as the modeling device is capable of endoscopic insertion.

At step 902, the balloon is positioned adjacent to the lesser curvature of the stomach 800, as shown in FIG. 11B. Once the balloon 880 is properly positioned within the stomach 800, the balloon 880 is inflated to the desired size through a tube or other means commonly known in the art. At step 904, under fluoroscopic or direct camera control, the distal end of the hollow casing 516 is advanced laparoscopically a patient's abdominal cavity. To achieve simultaneous delivery of the first and second bars 812, 816 of the gastric restriction device 802 to the posterior and anterior portions of the stomach 800, it may be necessary to perform a partial dissection of the greater gastric curvature epiploon prior to advancing to step 906.

As previously described with respect to the gastric restriction device 10, while the gastric restriction device 802 is positioned within the hollow casing 516, the first side 812A of the first bar 812 and the second side 816B of the second bar 816 are positioned adjacent to one another such that the magnets 820, 822 of each bar 812, 816 repel each other. At step 906, once the distal end of the hollow casing 516 is properly positioned within the abdominal cavity, the first and second arms 502, 506 are advanced through the hollow casing 516, thereby moving the gastric restriction device 802 through the distal end of the hollow casing 516 and into the abdominal cavity. Accordingly, the first side 812A of the first bar 812 is positioned adjacent to the anterior wall of the stomach 800 and the second side 816B of the second bar 816 is positioned adjacent to the posterior wall of the stomach 800. In addition, in one embodiment, the gastric restriction device 800 is positioned immediately adjacent to the portion of the stomach 880 containing the balloon 880.

Depending upon the indications of the particular patient, in positioning the gastric restriction device 802 on the stomach 800, it may be necessary for the clinician to perform a small dissection of the GEJ 857 to ensure the proper positioning of the proximal ends 813, 817 of the first and second bars 812, 816. Such dissection may occur at step 906 or prior thereto. In one embodiment, when the gastric restriction device 802 is properly positioned on the stomach 800, the distal ends 814, 818 of the first and second bars 812, 816, respectively, are located about 2 to about 4 centimeters above the pyloric area, thereby reserving a distal channel of the residual gastric pouch 860 to allow therefrom.

After the bars 812, 816 are sufficiently positioned relative to the stomach 800, the pins 826 of the first bar 812 are moved to the extended position at step 908. In one embodiment, at step 908 the pins 826 are extended by advancing the first arm 502 of the clamp device 500 distally, which thereby slidably moves the shaft 821 through the channel 824. In this manner, the shaft 821 applies downward pressure to the proximal ends 842 of the pins 826, which causes the pins 826 to move to the extended position. In at least one embodiment, after the shaft 821 has deployed the pins 826, the shaft 821 may be secured within the channel 824 by a locking mechanism (not shown) such that the pins 826 remain in the extended position. The locking mechanism may comprise a latching mechanism, a clip, a fastener, or any other mechanism that is capable of retaining the shaft 821 within the channel 824. In another embodiment, the dimensions of the shaft 821 can be manipulated to affect how far the pins 826 extend from the first side 12A of the first bar 12 as previously described with respect to method 700. It will be appreciated that step 908 may occur prior to step 906 such that the pins 826 of the first bar 812 are deployed prior to advancing the first and second arms 502, 506 through the hollow casing 516 and into the abdominal cavity. Further, in the embodiment wherein the gastric restriction device 802 comprises pins 826 that are fixed in the extended position, step 908 may be omitted from the method 900 altogether.

After the pins 826 are positioned in the extended position, the method 900 advances to step 910. At step 910, the gastric sleeve 850 and the residual gastric pouch 860 are formed. Specifically, the second arm 506 is rotated 180° such that the first side 816A of the second bar 816 is positioned adjacent to the anterior wall of the stomach 800. Accordingly, as the first side 816A of the second bar 816 comprises an opposite polarity of the first side 812A of the first bar 812, an attractive magnetic force is created, thereby causing the first bar 812 and the second bar 816 to move together and create the gastric sleeve 850 and the residual gastric pouch 860. The pins 826 extending from the first side 812A of the first bar 812 couple with the first side 816A of the second bar 816 through the stomach tissue and thus create pocks in the anterior and posterior walls of the stomach 800. In this manner, the pins 826 bear much of the load of the compression and maintain an interior area (not shown) between the bars 812, 816, within which the stomach resides.

After the gastric restriction device 802 is properly secured to the stomach 800, the clamp device 500 can be withdrawn at step 912. Specifically, at step 912, the first arm 502 and the second arm 506 are detached from the shaft 821 of the first bar 812 and the second bar 816, respectively. In the embodiment where the second bar 816 further comprises a hollow interior space (not shown), the second arm 506 is detached from the second bar 816 by rotating the second arm 506 and unscrewing the distal end 508 from the hollow interior space. In addition, the first arm 502 may be removed from the first bar 812 in much of the same manner. Further, the balloon 880 is withdrawn from the stomach, thus leaving an appropriately sized gastric sleeve 850.

The gastric remodeling devices disclosed herein and the clamp device 500 provide numerous benefits over the devices and systems of the prior art. The gastric remodeling device 10, 802 may be inserted laparoscopically, is minimally invasive, completely reversible and produces a reduced amount of negative side effects than the procedures of the prior art. In addition, the clamp device 500 allows the gastric remodeling device 10, 802 to be easily delivered in a procedure that takes as little as 10 minutes.

While various embodiments of devices, systems, and methods for restricting a stomach have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the intended scope. Indeed, this disclosure is not intended to be exhaustive or to limit the scope of the embodiments. The scope is to be defined by the appended claims, and by their equivalents.

Further, in describing representative embodiments, the disclosure may have presented a method and/or process as a particular sequence of steps. However, to the extent that the method or process docs not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present invention.

The invention claimed is:

1. A system for restricting the medically effective volume of a stomach, the system comprising:

an apparatus for restricting a stomach comprising:

a first bar having a proximal end, a distal end, a first side and a second side, the first bar comprising a first magnet, a first strap extending from the distal end of the first bar, at least one pin coupled with the proximal end of the first bar and at least one pin coupled with the distal end of the first bar, the pins of the first bar being moveable between a retracted position and an extended position, a channel extending from the proximal end of the first bar to the distal end of the first bar, and a shaft having a proximal end and a distal end, the distal end of the shaft configured to be slidably inserted into the channel and to apply a force to the pins of the first bar, the proximal end of the shaft releasably coupled with the first arm of the delivery device, wherein when the pins of the first bar are in the retracted position the pins are disposed within the channel of the first bar, and when the pins of the first bar are in the extended position the pins at least partially extend from the first bar; and a second bar having a proximal end, a distal end, a first side, a second side, and a hollow interior extending from the proximal end to the distal end, the second bar comprising a second magnet and a second strap separate and distinct from the first strap, the second strap extending from the distal end of the second bar, wherein the first side of the first bar is magnetically biased to attract the first side of the second bar and engage the stomach therebetween, the second side of the second bar is magnetically biased to repel the first side of the first bar, and the first strap of the first bar and the second strap of the second bar are configured to define an interior space when the first strap and the second strap are positioned proximate to each other; and a delivery device for facilitating the laparoscopic delivery of the apparatus for restricting the stomach, the delivery device comprising:

a first arm having a proximal end and a distal end, the distal end of the first arm configured to removably couple with the first bar, a second arm having a proximal end and a distal end, the second arm adapted for rotational movement, and the distal end of the second arm configured to removably couple with the hollow interior of the second bar, a lift system having a proximal end and a distal end, the proximal end of the lift system comprising an activation mechanism and the distal end of the lift system comprising a first branch coupled with the distal end of the first arm and a second branch coupled with the distal end of the second arm, and a hollow casing comprising an elongated tube having a proximal end, a distal end, and a hollow interior extending from the proximal end to the distal end, the distal end of the hollow casing adapted for laparoscopic introduction into a body, wherein the first arm, the second arm, and the lift system are slidably disposed within the hollow interior of the hollow casing, the first arm is adapted to move independently of the second arm, and operation of the second arm moves the second bar relative to the first bar and operation of the activation mechanism positions the first strap relative to the second strap such that the interior space is formed therebetween.

2. The system of claim 1, wherein the first arm of the delivery device is adapted for rotational movement.

3. The system of claim 2, wherein the distal end of the second arm of the delivery device comprises a screw-like tip and the hollow interior of the second bar is configured to receive the screw-like tip of the second arm.

4. The system of claim 1, wherein the second bar further comprises a longitudinal axis extending between the distal and proximal ends of the second bar and operation of the second arm rotates the second bar around the longitudinal axis of the second bar.

5. The system of claim 1, wherein the apparatus for restricting the stomach is disposed within the hollow casing of the delivery device such that the first side of the first bar is positioned adjacent to the second side of the second bar.

6. The system of claim 1, wherein the activation mechanism comprises a hand grip device comprising a trigger.

7. The system of claim 1, further comprising:

a balloon sized and shaped for insertion in a stomach;

wherein when the balloon is positioned to interact with the apparatus for restricting the stomach, the apparatus for restricting the stomach is operable to form a first gastric sleeve of a predetermined size.

8. A method for delivering an apparatus to a stomach comprising the steps of:

providing an apparatus for restricting a stomach comprising:

a first bar having a proximal end, a distal end, a first side, a second side, and a linear axis extended from the proximal end to the distal end, the first bar comprising a first magnet, a first strap extending from the distal end of the first bar, at least one pin coupled with the proximal end of the first bar and at least one pin coupled with the distal end of the first bar, the pins of the first bar being moveable between a retracted position and an extended position, a channel extending from the proximal end of the first bar to the distal end of the first bar, and a shaft having a proximal end and a distal end, the distal end of the shaft configured to be slidably inserted into the channel and to apply a force to the pins of the first bar, the proximal end of the shaft releasably coupled with the first arm of the delivery device, wherein when the pins of the first bar are in the retracted position the pins are disposed within the channel of the first bar, and when the pins of the first bar are in the extended position the pins at least partially extend from the first bar; and a second bar having a proximal end, a distal end, a first side, a second side, and a hollow interior extending at least partially between the proximal and distal ends, and the second bar comprising a second magnet and a second strap separate and distinct from the first strap, the second strap extending from the distal end of the second bar, wherein the first side of the first bar is magnetically biased to attract the first side of the second bar, the second side of the second bar is magnetically biased to repel the first side of the first bar, and the first strap of the first bar and the second strap of the second bar are configured to define an interior space when the first strap and the second strap are positioned proximate to each other;

providing a delivery device for facilitating the laparoscopic delivery of the apparatus for restricting the stomach, the delivery device comprising:

a first arm having a proximal end and a distal end, the distal end of the first arm configured to removably couple with the first bar, a second arm having a proximal end and a distal end, the second arm adapted for rotational movement, and the distal end of the second arm configured to removably couple with the hollow interior of the second bar, a lift system having a proximal end and a distal end, the proximal end of the lift system comprising an activation mechanism and the distal end of the lift system comprising a first branch coupled with the distal end of the first arm and a second branch coupled with the distal end of the second arm, and a hollow casing comprising an elongated tube having a proximal end, a distal end, and a hollow interior extending from the proximal end to the distal end, the distal end of the hollow casing capable of laparoscopic introduction into a body, wherein the first arm, the second arm, and the lift system are slidably disposed within the hollow interior of the hollow casing, the first arm is adapted to move independently of the second arm, operation of the second arm moves the second bar relative to the first bar, and operation of the activation mechanism positions the first strap relative to the second strap such that an interior space is formed therebetween;

inserting the distal end of the hollow casing laparoscopically into an abdomen;

positioning the first bar of the apparatus adjacent to an anterior surface of the stomach through the operation of the first arm of the delivery device;

forming a first gastric pouch and a second residual pouch by positioning the second magnet of the second bar adjacent to a posterior surface of the stomach such that the first magnet magnetically engages the second magnet through the stomach and the pins of the first bar engage the second bar;

positioning the first strap of the first bar relative to the second strap of the second bar and a lesser curvature of the stomach such that the interior space formed by the first and second straps forms a passageway between the first gastric pouch and the second residual pouch; and moving the pins of the first bar to the extended position.

9. The method of claim 8, wherein the first arm of the delivery device is adapted for rotational movement.

10. The method of claim 8, further comprising the steps of:
uncoupling the first arm of the delivery device from the first bar of the apparatus;
uncoupling the second arm of the delivery device from the second bar of the apparatus; and
withdrawing the delivery device from the abdomen.

11. The method of claim 10, wherein the distal end of the second arm of the delivery device further comprises a screw-like tip and the hollow interior of the second bar is configured to receive the screw-like tip of the second arm, and the step of uncoupling the second arm of the delivery device from the second bar of the apparatus further comprises the step of unscrewing the screw-like tip of the second arm from the hollow interior of the second bar.

12. The method of claim 8, wherein the step of moving the pins of the first bar to the extended position further comprises operating the shaft to apply the force to at least one of the pins of the first bar.

13. The method of claim 12, wherein the step of moving the pins of the first bar to the extended position further comprises the step of:
operating the first arm of the delivery device to cause the shaft to slidably advance through the channel.

14. The method of claim 8, wherein the step of forming a first gastric pouch and a second residual pouch further comprises the steps of:
advancing the second bar through the hollow casing through the operation of the second arm of the delivery device;
positioning the second bar adjacent to the posterior surface of the stomach; and
rotating the second bar through operation of the second arm such that the first side of the second bar magnetically engages the first side of the first bar through the stomach.

15. The method of claim 14, wherein the second bar further comprises a longitudinal axis extending between the distal and proximal ends of the second bar and operation of the second arm rotates the second bar around the longitudinal axis of the second bar.

16. The method of claim 8, wherein the step of positioning the first strap of the first bar relative to the second strap of the second bar and a lesser curvature of the stomach such that the interior space formed by the first and second straps forms a passageway between the first gastric pouch and the second residual pouch further comprises the step of:
operating the lift system to maneuver the second bar in a direction transverse to the linear axis of the first bar such that the passageway comprises a diameter.

17. The method of claim 16, wherein the activation mechanism of the lift system further comprises a hand grip device comprising a trigger, and the step of operating the lift system to maneuver the second bar in a direction transverse to the linear axis of the first bar such that the passageway within the stomach comprises a diameter further comprises the step of pulling the trigger of the hand grip device.

18. The method of claim 8, wherein the second bar further comprises a longitudinal axis extending between the distal and proximal ends of the second bar and operation of the second arm rotates the second bar around the longitudinal axis of the second bar.

19. The method of claim 8, further comprising the steps of:
positioning a balloon within the stomach in a location adjacent to the lesser curvature of the stomach; and
using the balloon to position the first bar and the second bar on the stomach, thereby forming a first gastric sleeve of a predetermined size.

20. A method for delivering an apparatus to a stomach comprising the steps of:
providing an apparatus for restricting a stomach comprising:
a first bar having a proximal end and a distal end, the first bar comprising a first magnet, at least one pin coupled with the proximal end of the first bar, at least one pin coupled with the distal end of the first bar, the pins of the first bar being moveable between a retracted position and an extended position, a channel extending from the proximal end of the first bar to the distal end of the first bar, and a shaft having a proximal end and a distal end, the distal end of the shaft configured to be slidably inserted into the channel and to apply a force to the pins of the first bar, the proximal end of the shaft releasably coupled with the first arm of the delivery device, wherein when the pins of the first bar are in the retracted position the pins are disposed within the channel of the first bar, and when the pins of the first bar are in the extended position the pins at least partially extend from the first bar, and a second bar having a proximal end and a distal end,
wherein a portion of the first magnet is magnetically biased to attract a portion of the second magnet and engage the stomach therebetween;
providing a delivery device for facilitating the laparoscopic delivery of the apparatus for restricting the stomach, the delivery device comprising:
a first arm having a proximal end and a distal end, the distal end of the first arm removably coupled with the first bar,
a second arm having a proximal end and a distal end, the second arm adapted for rotational movement, and the distal end of the second arm removably coupled with the hollow interior of the second bar,
a lift system having a proximal end and a distal end, the proximal end of the lift system comprising an activation mechanism and the distal end of the lift system comprising a first branch coupled with the distal end of the first arm and a second branch coupled with the distal end of the second arm, and
a hollow casing comprising an elongated tube having a proximal end, a distal end, and a hollow interior extending from the proximal end to the distal end, the distal end of the hollow casing configured for laparoscopic introduction into a body,
wherein the first arm, the second arm, and the lift system are slidably disposed within the hollow interior of the hollow casing, the first arm is adapted to move independently of the second arm, and operation of the second arm moves the second bar relative to the first bar;
inserting the distal end of the hollow casing laparoscopically into an abdomen;
positioning the first bar of the apparatus adjacent to an anterior surface of the stomach through the operation of the first arm of the delivery device;
positioning the second bar adjacent to a posterior surface of the stomach through operation of the second arm of the delivery device such that the first magnet of the first bar magnetically engages the second magnet of the second bar through the stomach, the pins of the first bar engage the second bar, and the stomach is restricted to form a first gastric sleeve and a second residual pouch are formed; and
moving the pins of the first bar to the extended position.

21. The method of claim 20, wherein the first arm of the delivery device is adapted for rotational movement.

22. The method of claim 20, further comprising the steps of:
uncoupling the first arm of the delivery device from the first bar of the apparatus;
uncoupling the second arm of the delivery device from the second bar of the apparatus; and
withdrawing the delivery device from the abdomen.

23. The method of claim 22, wherein the distal end of the second arm of the delivery device further comprises a screw-like tip and the hollow interior of the second bar is configured to receive the screw-like tip of the second arm, and the step of uncoupling the second arm of the delivery device from the second bar of the apparatus further comprises the step of unscrewing the screw-like tip of the second arm from the hollow interior of the second bar.

24. The method of claim 20, wherein each of the at least one pins is adapted to move from the retracted position to the extended position when the force is applied by the shaft.

25. The method of claim 24, wherein the step of moving the pins of the first bar to the extended position further comprises the step of:
advancing the shaft through the channel and applying the force to the pins through operation of the first arm of the delivery device.

26. The method of claim 20, wherein the step of positioning the second bar adjacent to a posterior surface of the stomach further comprises the steps of:
advancing the second bar through the hollow casing through the operation of the second arm of the delivery device;
positioning the second bar adjacent to the posterior surface of the stomach; and
rotating the second bar through operation of the second arm such that the first side of the second bar magnetically engages the first side of the first bar through the stomach.

27. The method of claim 26, wherein the second bar further comprises a longitudinal axis extending between the distal and proximal ends of the second bar and operation of the second arm rotates the second bar around the longitudinal axis of the second bar.

28. The method of claim 20, further comprising the steps of:
positioning a balloon within the stomach in a location adjacent to the lesser curvature of the stomach; and
using the balloon to position the first bar and the second bar on the stomach, thereby forming a first gastric sleeve of a predetermined size.

29. The method of claim 20, wherein the second bar further comprises a longitudinal axis extending between the distal and proximal ends of the second bar and operation of the second arm rotates the second bar around the longitudinal axis of the second bar.

30. A system for restricting the medically effective volume of a stomach, the system comprising:
an apparatus for restricting a stomach comprising:
a first bar having a proximal end, a distal end, a first side and a second side, the first bar comprising a first magnet, a first strap extending from the distal end of the first bar, at least one pin coupled with the proximal end of the first bar and at least one pin coupled with the distal end of the first bar, the pins of the first bar being moveable between a retracted position and an extended position, a channel extending from the proximal end of the first bar to the distal end of the first bar, and a shaft having a proximal end and a distal end, the distal end of the shaft configured to be slidably inserted into the channel and to apply a force to the pins of the first bar, the proximal end of the shaft releasably coupled with the first arm of the delivery device, wherein when the pins of the first bar are in the retracted position the pins are disposed within the channel of the first bar, and when the pins of the first bar are in the extended position the pins at least partially extend from the first bar; and
a second bar having a proximal end, a distal end, a first side, a second side, and a hollow interior extending from the proximal end to the distal end, the second bar comprising a second magnet and a second strap separate and distinct from the first strap, the second strap extending from the distal end of the second bar, the second bar further comprises a longitudinal axis extending between the distal and proximal ends of the second bar and operation of the second arm rotates the second bar around the longitudinal axis of the second bar, wherein the first side of the first bar is magnetically biased to attract the first side of the second bar and engage the stomach therebetween, the second side of the second bar is magnetically biased to repel the first side of the first bar, and the first strap of the first bar and the second strap of the second bar are configured to define an interior space when the first strap and the second strap are positioned proximate to each other; and a delivery device for facilitating the laparoscopic delivery of the apparatus for restricting the stomach, the delivery device comprising:

a first arm having a proximal end and a distal end, the distal end of the first arm configured to removably couple with the first bar and adapted for rotational movement, a second arm having a proximal end and a distal end, the second arm adapted for rotational movement, the distal end of the second arm of the delivery device comprises a screw-like tip and the hollow interior of the second bar is configured to receive the screw-like tip of the second arm, and the distal end of the second arm configured to removably couple with the hollow interior of the second bar, a lift system having a proximal end and a distal end, the proximal end of the lift system comprising an activation mechanism and the distal end of the lift system comprising a first branch coupled with the distal end of the first arm and a second branch coupled with the distal end of the second arm, and a hollow casing comprising an elongated tube having a proximal end, a distal end, and a hollow interior extending from the proximal end to the distal end, the distal end of the hollow casing adapted for laparoscopic introduction into a body, wherein the first arm, the second arm, and the lift system are slidably disposed within the hollow interior of the hollow casing, the first arm is adapted to move independently of the second arm, and operation of the second arm moves the second bar relative to the first bar and operation of the activation mechanism positions the first strap relative to the second strap such that the interior space is formed therebetween.

31. The system of claim 30, further comprising:

a balloon sized and shaped for insertion in a stomach;

wherein when the balloon is positioned to interact with the apparatus for restricting the stomach, the apparatus for restricting the stomach is operable to form a first gastric sleeve of a predetermined size.

\* \* \* \* \*